United States Patent [19]

Yamauchi et al.

[11] Patent Number: 5,519,330

[45] Date of Patent: May 21, 1996

[54] METHOD AND APPARATUS FOR MEASURING DEGREE OF CORROSION OF METAL MATERIALS

[75] Inventors: Hiroshi Yamauchi; Masanori Sakai; Katsumi Mabuchi; Takuya Takahashi, all of Hitachi; Noriyuki Ohnaka, Katsuta; Shigeo Hattori, Ibaraki, all of Japan

[73] Assignee: Hitachi, Ltd., Tokyo, Japan

[21] Appl. No.: 126,768

[22] Filed: Sep. 27, 1993

[30] Foreign Application Priority Data

Sep. 28, 1992 [JP] Japan .................................. 4-258660

[51] Int. Cl.$^6$ ................................................. G01N 27/06
[52] U.S. Cl. ........................ 324/700; 324/425; 324/713; 324/71.2; 204/404
[58] Field of Search ........................... 204/153.1, 153.11, 204/400, 404, 406; 324/71.2, 71.1, 425, 693, 700, 710, 713, 718

[56] References Cited

U.S. PATENT DOCUMENTS

| | | | |
|---|---|---|---|
| 4,065,373 | 12/1977 | Martin et al. | 204/195 C |
| 4,179,349 | 12/1979 | Park | 204/195 R |
| 4,395,318 | 7/1983 | Tait et al. | 204/404 |
| 4,518,464 | 5/1985 | Takahashi et al. | 204/400 |
| 4,564,422 | 1/1986 | Simoneau et al. | 204/400 |
| 4,564,436 | 1/1986 | Buzzanca et al. | 204/400 |
| 4,937,038 | 6/1990 | Sakai et al. | 204/153.1 |
| 5,316,663 | 5/1994 | Sakai et al. | 204/404 |

FOREIGN PATENT DOCUMENTS 2349833 of 0000 France .
57028246 of 0000 Japan .

OTHER PUBLICATIONS

Journal of the Electrochemical Society vol. 124, No. 5, May 1977, Manchester, New Hampshire US, pp. 656–661, K. Boto et al, "The determination of the corrosion rate of zinc in solution by the differential pulse method".

Journal of the Electrochemical Society vol. 127, No. 8, Aug. 1980, Manchester, New Hampshire US, pp. 1706–1709, L. Williams, "Automatic corrosion rate monitoring of metals in solution".

Journal of the Electrochemical Society vol. 135, No. 3, Mar. 1988, Manchester, New Hampshire US, pp. 783–784, O. Lev et al, "The application of scanning tunneling microscopy to in situ studies of nickel electrodes under potential control".

Anticorrosion Technology 29, pp. 163–169 (1980), month unavailable, Umemura et al, "Evaluation of IGSCC Susceptibility of Austenitic Stainless Steels Using Electrochemical Reactivation Method".

Primary Examiner—Kenneth A. Wieder
Assistant Examiner—Glenn W. Brown
Attorney, Agent, or Firm—Antonelli, Terry, Stout & Kraus

[57] ABSTRACT

A corrosion degree measuring method capable of field measurement for intergranular corrosion, particularly the sensitization degree, of the plant's structural materials in a narrow space. The metal electrode made of a material being measured and the counter electrode to the metal electrode are immersed in an electrolytic solution. A voltage is applied to the metal electrode in the anodic direction so as to raise the potential of the metal electrode up to the passive state potential and to keep the metal electrode at the passive state potential. The passive state potential is used as a reference potential, and a pulse-like potential signal is applied to the metal electrode in the cathodic direction. At the time of the application of the pulse potential signal, a current between the metal electrode and the counter electrode is measured, and the corrosion degree of the material being measured is determined from the intensity of the current.

56 Claims, 13 Drawing Sheets

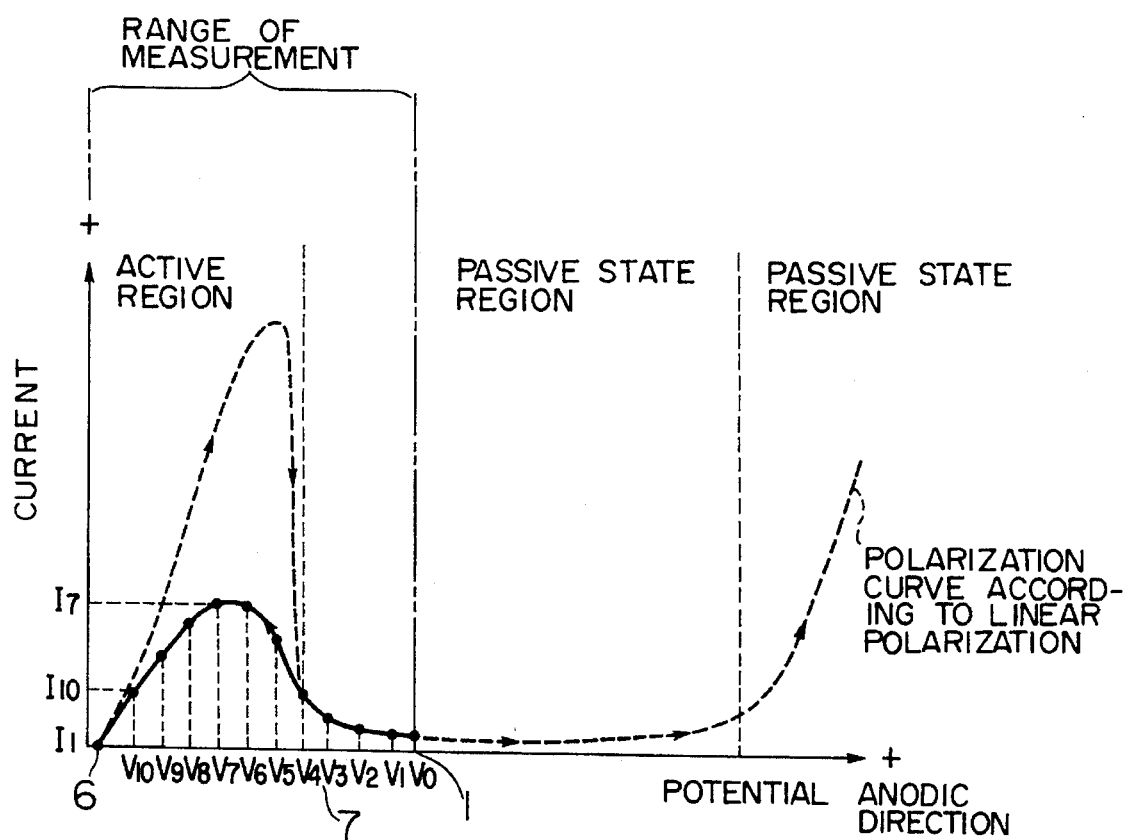
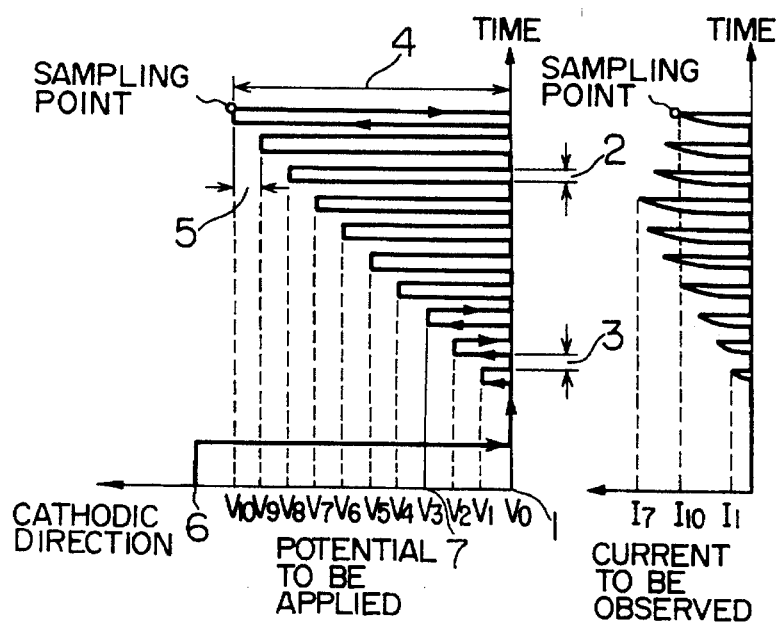

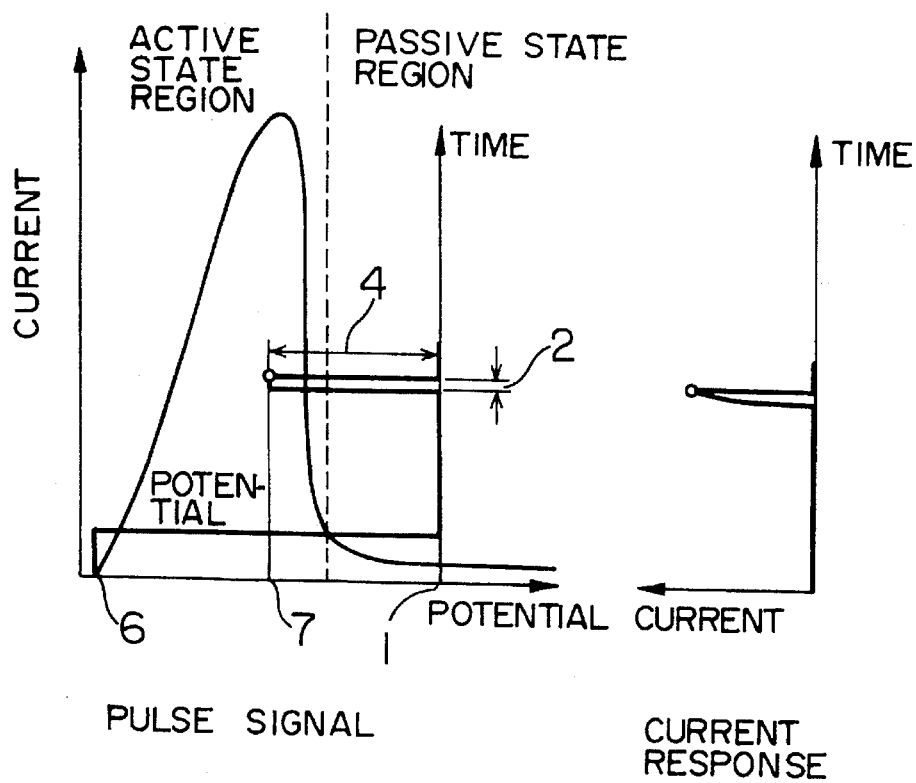
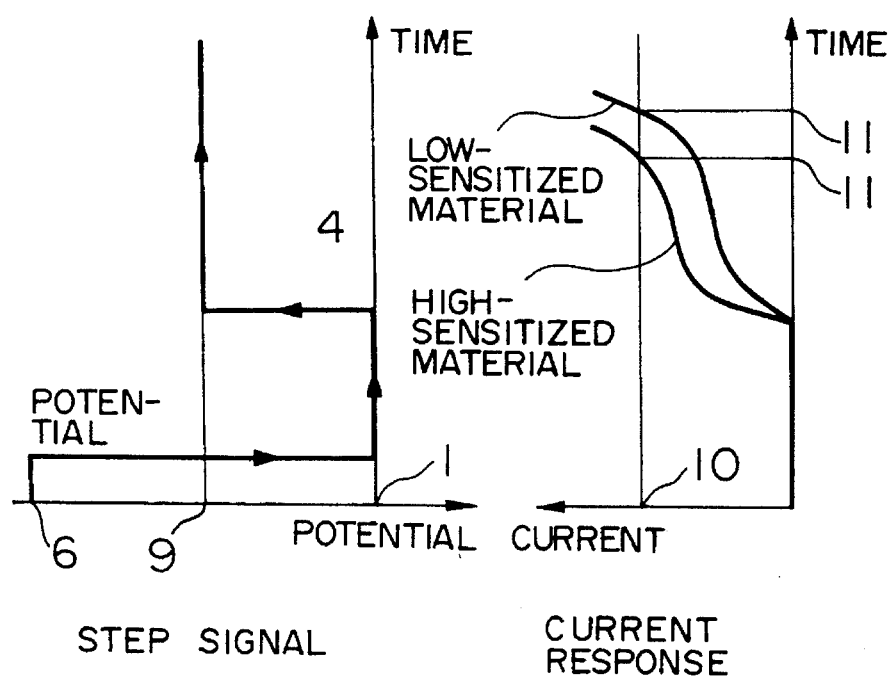

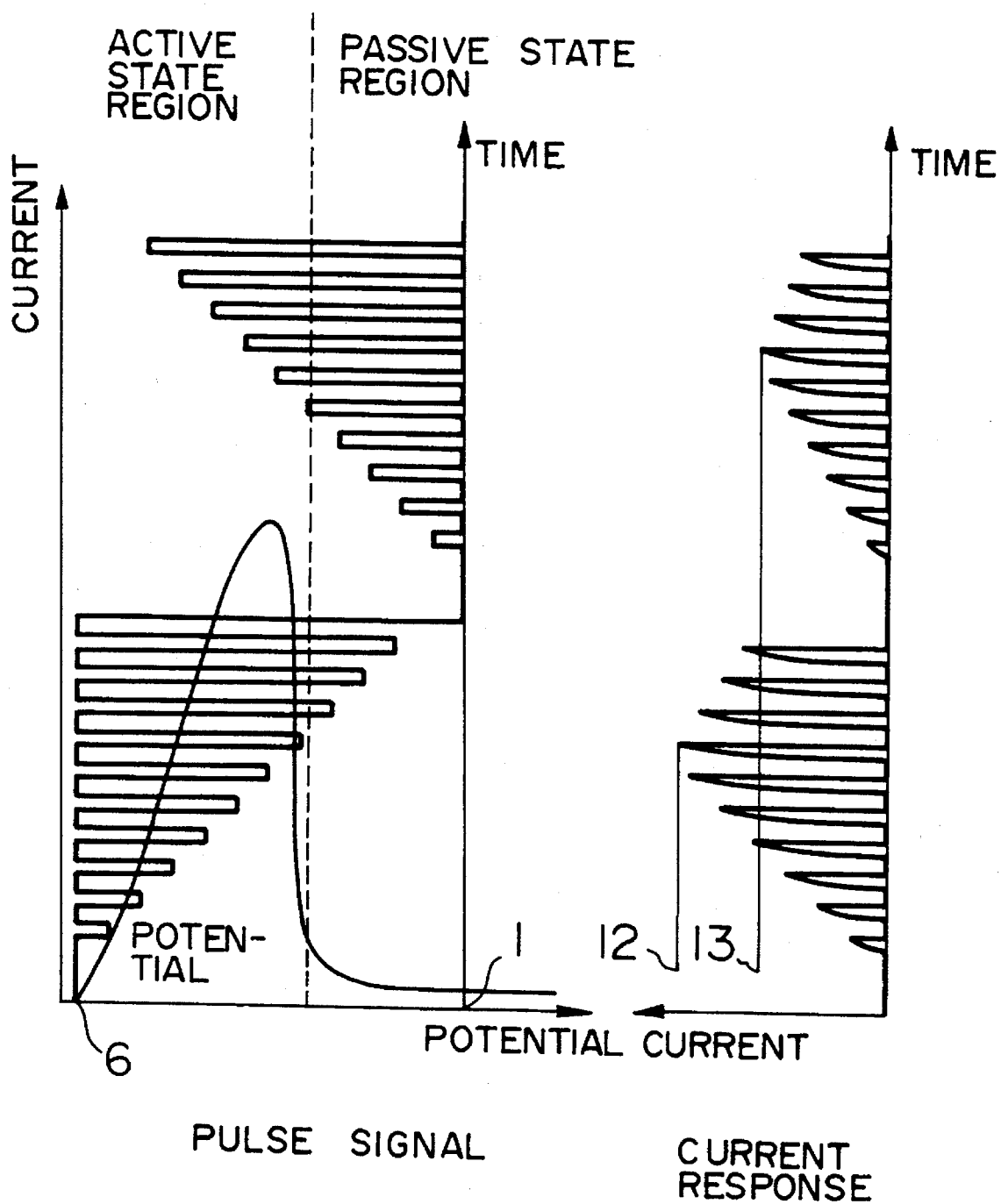

FIG.8A
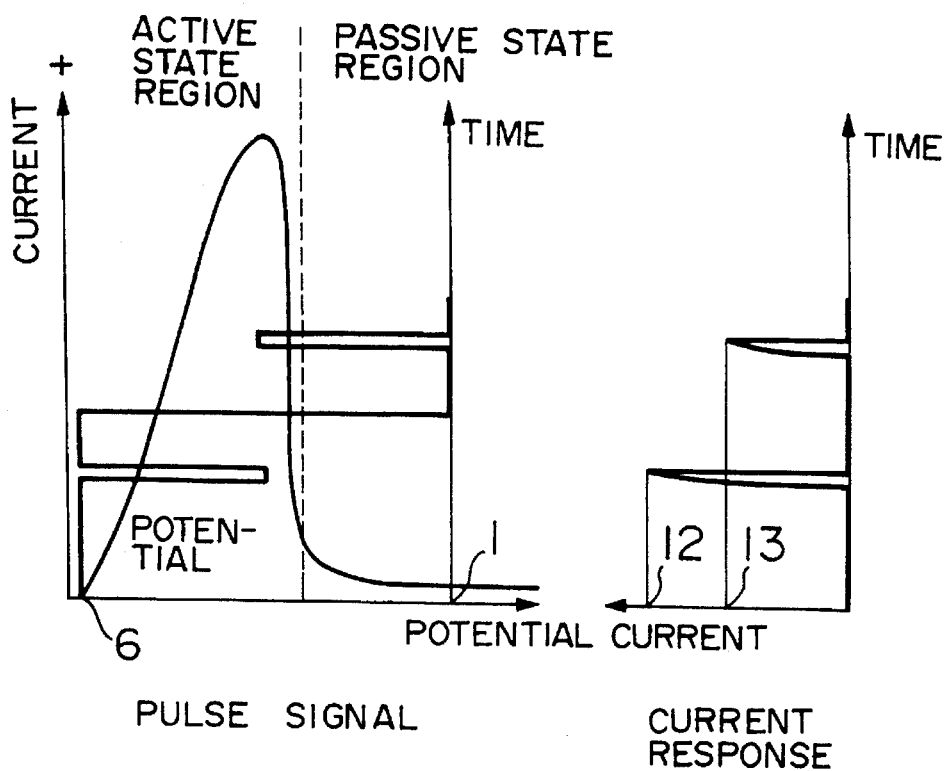
PULSE SIGNAL
FIG.8B
CURRENT RESPONSE
FIG.9A
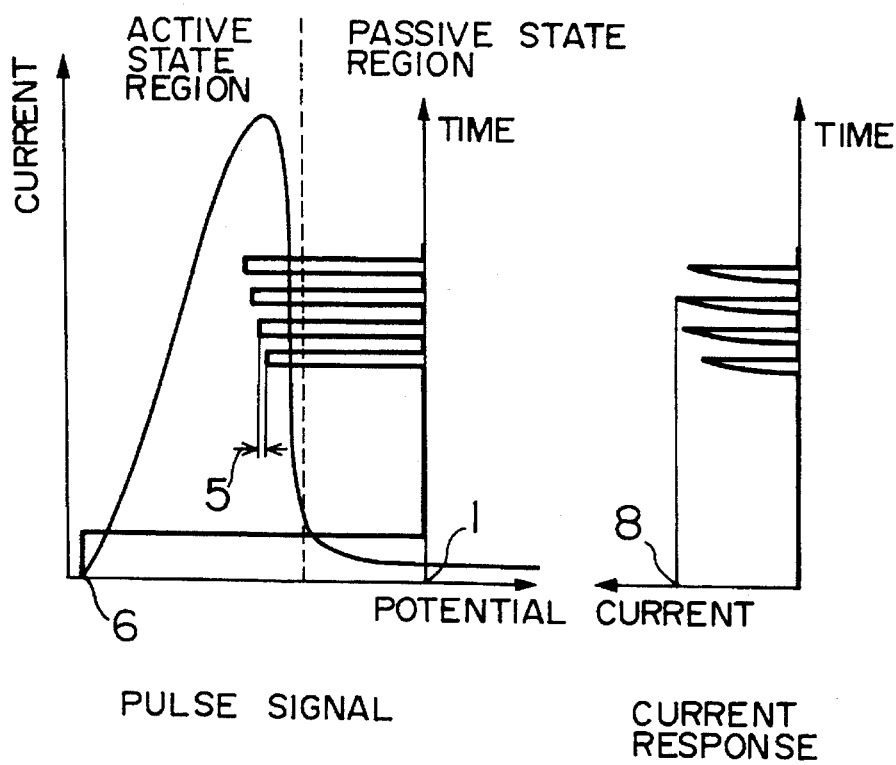
PULSE SIGNAL
FIG.9B
CURRENT RESPONSE

METHOD AND APPARATUS FOR MEASURING DEGREE OF CORROSION OF METAL MATERIALS

BACKGROUND OF THE INVENTION

This invention relates to a method of detecting the degree of corrosion of metal materials, and particularly to a method of detecting the degree of corrosion of metal materials of which power plants, chemical plants and so on are made or of metal materials of which semiconductors, thin films, wiring conductors and so on are made in the information industry.

The method of detecting the intergranular corrosion is variously described in "ANTICORROSION TECHNOLOGY HANDBOOK" (edited by ANTICORROSION ASSOCIATION, and published by NIKKAN KOGYO SHINBUNSHA). For example, there are the oxalic acid etching test for determining the intergranular corrosion resistance from the etched texture caused by electrolytic etching in a 10-% oxalic acid solution, the sulfuric acid/ferric sulfate corrosion test for determining the degree of corrosion from the weight loss after the object being tested is immersed in a boiled 50-% sulfuric acid+ ferric sulfate solution for 120 hours, the nitric acid/fluoric acid corrosion test for determining the degree of corrosion from the weight loss after the object being tested is immersed in a 10-% nitric acid + 3-% fluoric acid solution at 70° C. for two hours, the nitric acid corrosion test for determining the degree of corrosion from the weight loss after the object being tested is immersed in a boiled 65-% nitric acid for 48 hours, the sulfuric acid/copper sulfate corrosion test for determining the degree of corrosion from the presence or absence of cracks after the object being tested is immersed in a boiled 15.7-% sulfuric acid+ 5.5-% copper sulfate+ pieces of copper solution for 16 hours and bent for opening processing, and the electrochemical potentiokinetic reactivation test (EPR method) for determining the degree of corrosion from the ratio of going and returning peak currents which can be obtained by the measurement of the going and returning polarization curves in a 0.5-M sulfuric acid+ 0.01-M potassium thiocyanate solution at 30° C. These tests are standardized by JIS (Japanese Industrial Standard).

Of these tests, the EPR is a nondestructive evaluation method as reported in "ANTICORROSION TECHNOLOGY" 29, pp. 163–169 (1980) and is excellent over the other tests because the determination of sensitization degree can be made in a relatively short time. This test, for these reasons, is used for detecting the corrosion of materials of which an actual plant is made.

The EPR is the method of interdetecting the intergranular corrosion, particularly the degree of sensitization, or the phenomenon in which the chromium concentration is reduced in the grain boundary due to formation of the chromium carbide which is produced by the segregation of carbon into the grain boundary when stainless steel or the like is heated. In the EPR, a metal sample of which the corrosion degree is desired to evaluate is immersed as electrodes in a volume, 200 cm³ or above of a 0.5-M sulfuric acid + 0.01-M potassium thiocyanate solution at 30° C. Then, the sample is applied with a range of potential from the corrosion potential to 0.300 V vs. SHE scanned in the master or anodic direction and immediately back to the corrosion potential in the slave or cathodic direction at a linear polarization speed of 100± 5 mV/min as an electrochemical measurement condition. The degree of sensitization is determined by the ratio between the current flowing at the time of voltage application in the anodic (going) direction and the current flowing at the time of voltage application in the cathodic (returning) direction, or by the reactivation rate as expressed as follows.

Reactivation rate % =

((maximum anode current in the returning direction)/

(maximum anode current in the going direction)) × 100.

Thus, the EPR needs a volume of solution cell, 200 cm³, measuring time of 5 minutes, and an amount of electricity, 10 through 15 C/cm².

SUMMARY OF THE INVENTION

When the metal materials of which an actual plant is made are nondestructively tested for their corroded state according to the conventional EPR, a solution cell of 200 cm³ or above must be placed around the portion being evaluated in order that the portion being tested can be immersed in the solution cell. However, many plants actually often have only a small space around the portion being evaluated. If the metal of which a thin pipe is made is necessary to evaluate for its corroded state within the inside of the pipe or if a component being tested is of the components which are packaged at a high density within a plant, the solution cell of 200 cm³ or above cannot be inserted around the portion being evaluated, or the EPR cannot be used.

In order to solve this problem, if in the EPR only the cell is made small in size so that the amount of solution can be reduced with the other conditions unchanged, the composition of the solution is greatly changed upon measurement by the consumption of electrolytic components, generation of gas and production of metal ions due to the electrolysis in the solution. As a result, the reliability of the measurement is lost.

In addition, the conventional EPR has a low detection sensitivity for low-sensitization degree samples.

It is an object of the invention to provide a corrosion degree measuring method capable of sensitively detecting the intergranular corrosion sensitivity within a narrow place such as a small or thin pipe.

In order to achieve the above object, according to the first aspect of the invention, there is provided a method of measuring the corrosion degree of a material being measured by immersing a metal electrode made of the material being measured and a counter electrode connected to the metal electrode in an electrolytic solution, applying a voltage to the metal electrode, measuring a current flowing between the metal electrode and the counter electrode, and determining the corrosion degree of the material being measured, comprising the steps of:

applying a voltage changing in an anodic direction to the metal electrode which is at an initial or corrosion potential when the metal electrode is immersed in the electrolytic solution, so that the potential of the metal electrode is raised up to a passive state potential at which the material being measured reaches a passive state region, and is kept at the passive state potential; and applying a pulse-like voltage signal changing in a cathodic direction to the metal electrode which is kept at the passive state potential, measuring a current flowing between the metal electrode and the counter electrode at the time of the pulse voltage application, and determining the corrosion degree of the material being measured from the current intensity.

The pulse-like voltage signal changing in the cathodic direction may be formed of a plurality of pulse-like voltage signals of different pulse potentials, which are applied in order, and the largest one of the current values measured when the plurality of pulse-like voltage signals are applied is selected and used for determining the corrosion degree.

The pulse-like voltage signal changing in the cathodic direction may be formed of a single pulse-like voltage signal having a predetermined pulse potential.

The measured magnitude of the current may be divided by the surface area of the metal electrode to obtain a current density, and the corrosion degree of the material may be determined from the current density.

According to the second aspect of the invention there is provided a method of measuring the corrosion degree of a material being measured by immersing a metal electrode made of the material being measured and a counter electrode connected to the metal electrode in an electrolytic solution, applying a voltage to the metal electrode, measuring a current flowing between the metal electrode and the counter electrode, and determining the corrosion degree of the material being measured, comprising the steps of:

applying a voltage changing in an anodic direction to the metal electrode which is at an initial potential when the metal electrode is immersed in the electrolytic solution, so that the potential of the metal electrode is raised up to a passive state region, and is kept at the passive state region; and stepwise changing the potential of the metal electrode up to a predetermined potential which lies between the initial potential and the passive state potential, measuring the time in which the value of a current flowing between the metal electrode and the counter electrode at that time reaches a constant value, and determining the corrosion degree of the material from the time.

The time measured for the material and the time measured for a reference material having a known intergranular corrosion degree can be compared with each other to determine the intergranular corrosion degree of the material being measured.

According to the third aspect of the invention there is provided a method of measuring the corrosion degree of a material being measured by immersing a metal electrode made of the material being measured and a counter electrode connected to the metal electrode in an electrolytic solution, applying a voltage to the metal electrode, measuring a current flowing between the metal electrode and the counter electrode, and determining the corrosion degree of the material being measured, comprising the steps of:

applying a voltage changing in an anodic direction to the metal electrode which is at an initial potential when the metal electrode is immersed in the electrolytic solution, so that the potential of the metal electrode is raised up to a passive state potential at which the material being measured reaches a passive state region, and is kept at the passive state potential;

applying a pulse-like voltage signal which changes in a cathodic direction and of which the peak potential lies in an active state region to the metal electrode which is kept at the passive state potential, and measuring a current flowing between the metal electrode and the counter electrode when the pulse voltage is applied in the cathodic direction;

applying a pulse-like signal which changes in an anodic direction and of which the peak potential lies in an transpassive state region to the metal electrode which is kept at the passive state potential as the reference potential, and measuring a current between the metal electrode and the counter electrode when the pulse voltage is applied in the anodic direction;

comparing the current measured for the material being measured when the pulse voltage is applied in the cathodic direction, and the current measured for a reference material having a known sensitization degree when the pulse voltage is applied in the cathodic direction so as to determine the sensitization degree of the material being measured; and comparing the current measured for the material being measured when the pulse voltage is applied in the anodic direction, and the current measured for a reference material having a known intergranular corrosion degree when the pulse voltage is applied in the anodic direction so as to determine the intergranular corrosion degree of the material being measured.

According to another aspect of the invention, there is provided a water quality control system having means for controlling the quality of water in the water cooling system for a nuclear plant, including an electrode housing of an electrolytic cell provided at a constitutional member which is made in contact with the cooling water, a voltage source for applying a pulse potential which has a certain parameter for a reference electrode voltage to the constitutional member within the nuclear reactor, a signal source for supplying to the voltage source a potential for active state region or transpassive state region after the constitutional member is kept at a passive state potential, a memory for storing the intensity of a current flowing on the basis of a signal from the voltage source, a current processor for processing data stored in the memory to determine a current value or peak current value, a calculator for calculating the corrosion resistance of the constitutional member on the basis of the determined current value or peak current value, and the means for controlling the quality of the cooling water on the basis of the information from the calculator.

This invention has a comparator for comparing the result from the calculator with a reference value. Thus, the water quality can be controlled on the basis of the information from the comparator. When the result exceeds the reference value, an alarm is issued to thereby make preventive maintenance. This invention can be applied to the BWR and PWR of a nuclear plant, and used for the diagnosis of the material of which a steam power generation plant or chemical plant is made and which is exposed to high-temperature and high-pressure water.

The technique for detecting the intergranular corrosion sensitivity including the sensitization phenomenon of metal materials is absolutely necessary in determining the reliability and life time of the material of a structure being examined. Particularly if the sensitization degree of a plant under operation can be grasped, it will be advantageous in the prevention of failures and accidents and the maintenance. The technique for measuring in a narrow space is most important.

In order to make it possible to measure in a narrow space such as a thin pipe, it is necessary to reduce the size of the cell which holds the electrolytic solution for electrochemical measurement. In the conventional measuring technique, however, a large volume of electrolyte is necessary to obtain the information on the intergranular corrosion sensitivity. Thus, when a small cell is used, various substances are generated in the electrolytic solution because of the consumption of electrolytic components, production of gases and metal ions and so on, loosing the reliability of measured values. To solve this problem, this invention proposed a intergranular corrosion measuring method in which the electrolysis time is short and the volume of electrochemical cell is very small.

The electrochemical properties of a metal material, for example, a stainless steel will be described briefly. The stainless steel in a low-pH solution of sulfuric acid or others electrochemically takes three states of active region, passive state region and transpassive state region. First, when the stainless steel is immersed in a low-pH solution, the passive film on the surface is destroyed, and hence the stainless steel is in an active dissolving state. The potential (corrosion potential) of the stainless steel under this condition is changed by applying a scan voltage, which changes in the master direction (anodic, +direction), from the external power supply to the stainless steel. At this time, if the linear polarization method is used in which the potential is linearly swept from the corrosion potential, an anodic current based on the active dissolution is observed. When the potential is further shifted in the anodic direction, a potential region appears in which the current is suddenly reduced by several figures. This is because a metal oxide film of a nondissolve oxide or hydroxide or oxyhydroxide, called the passive film is formed on the surface of the stainless steel, preventing the metal from dissolving. Then, when the potential is further shifted, a region continues in which a current of the same level as or smaller level than at the start of the passive state is substantially constant irrespective of the potential change. This current value is necessary for holding or maintaining the passive state, and called the passive state holding current. When the potential is further shifted, the transpassive state region appears in which the current again increases at a certain potential. The current in the transpassive state region is based on the dissolution of trivalent ions of iron, and/or sexivalent ions of chromium and/or the production of oxygen in electrolysis of water.

The action of the corrosion degree measuring method according to the first aspect of the invention will be described below. When a sample electrode made of a material being measured is immersed for a while in an electrolytic solution, the sample electrode starts active dissolution as described above. Then, the potential is stepwise shifted up to the passive state region by the external power supply. Thus, the passive film is formed, suppressing the active dissolution reaction. Then, a pulse signal changing in the cathodic direction is applied to the test electrode which is maintained at the initial potential by which it is changed to the passive state region. At this time, the current density observed when the pulse signal is applied is measured.

According to this method, when the potential is shifted from the corrosion potential to the potential for the passive state region where it is made passive, and then changed to the active region, corrosion potential, the film on the intergranular portion cannot be maintained in the passive state. Thus, the dissolution reaction of the intergranular portion selectively progresses, and the resulting current is observed. The other surface than the intergranular portion is covered with a chromium-rich film, and thus does not dissolve.

The reason why the dissolution reaction selectively progresses on the intergranular portion is that the passive film on the intergranular portion which is exposed to the metal surface has poor corrosion resistance. It is known that, for example, a sensitized material of SUS304 type containing about 0.05 wt % of carbon has its chromium content reduced to 12% of the chromium content under which the passive state can be maintained stably because the chromium carbide is deposited.

The solution-annealed material has no chromium carbide produced at the intergranular portion. Therefore, even if the pulse signal is applied to the active region, this material is not dissolved because it is covered with a uniform corrosion resistance film. Thus, no current based on the dissolution reaction is observed. According to this invention, the sensitization of a material can be known from the relation of whether the measured current is large or not.

In addition, a plurality of pulse signals with different pulse potentials may be applied as the pulse signal being applied. If a series of pulses of which the pulse height is gradually increased from the initial potential to the corrosion potential in the cathodic direction is applied to, for example, the stainless steel of SUS304 which was subjected to a sensitization process of 600° C., 24 hours, and at this time if the current density at each pulse is measured, the maximum current value is obtained at the potential substantially equal to that at which the largest current is observed at the time of active dissolution, or at the potential shifted about several hundred mV in the cathodic direction. Under the same conditions, when a measurement is made of the test electrode which was subjected to a solution-annealed process of 1050° C., 0.5 hour, no current is observed, and thus the peak current is considerably reduced. Therefore, a plurality of pulses can be applied, and the largest one of the obtained current values can be selected.

If the potential at which the maximum current value is observed and the potential at which different current values are observed for different materials are previously known by an experiment using a series of pulses, a single pulse with a peak potential may be applied in place of the series of pulses.

In the corrosion degree measuring method according to the second aspect of the invention, the potential on the electrode is stepwise changed from the initial potential to a certain potential. Thus, since the current value increases with time, the time taken until the current reaches a constant value is measured for each material. Since the material of which the passive film has a low corrosion resistance is fast destroyed in its film, the material having a low corrosion resistance film such as a sensitized material reaches a constant current value in a short time. The inventors observed that when the current value was in the range from 0.01 to 3 mA/cm$^2$, the materials exhibited a clear difference among the measured time intervals. In addition, the greatest current difference was obtained at a potential of 0.100± 0.050 V where a peak current is observed.

In the corrosion degree measuring method according to the third aspect of the invention, information on sensitization can be obtained from the pulse signal which changes from the initial potential for the passive state region in the cathodic direction, while information on intergranular corrosion resistance in the transpassive state region can be obtained from the pulse signal which changes in the anodic direction. The total intergranular corrosion characteristics can be simultaneously obtained by continuously applying the pulse signal.

The technology for detecting the corrosion resistance, particularly the sensitization degree or the like corresponding to the intergranular corrosion crack sensitivity of the material of which a plant is made, at the time of regular checking during the operation of the plant, is concerned with the evaluation standard for the materials reliability itself. The result of the sensitization degree evaluation for the object being monitored is directly coupled to the operation management schedule itself from the plant maintenance point of view. From the operating plant maintenance point of view, it is desired to develop the technology capable of the field test of the object being widely monitored, and quickly obtaining the results of the health evaluation of the working material of which the plant is made. The fundamental techniques necessary for this technology can be roughly divided into three techniques: 1) evaluation and detection can be made at a very fine, narrow pipe or space, 2) measurement of the object being widely monitored can be made in a short time, and 3) the object being measured can be scanned by remote control.

This invention has achieved the above three technical subjects by the following means. First, in order that evaluation and detection can be made at a very fine, narrow pipe or space as at 1), it is necessary to design a very small cell for electrochemical measurement. To achieve this very small cell, the amount of current flowing in the electrochemical cell must be reduced so that the amount of generation of substances and gases in the electrolytic solution can be reduced as much as possible, and the sensitization degree of the object being monitored must be detected.

BRIEF DESCRIPTION OF THE DRAWINGS

FIGS. 1A, 1B and 1C are graphs showing measuring conditions and measured results in the corrosion degree detecting method of the first embodiment of the invention.

FIGS. 4A and 4B are graphs showing measuring conditions and measured results in the corrosion degree detecting method using a single pulse signal according to the first embodiment of the invention.

FIGS. 5A and 5B are graphs showing the measuring conditions and measured results in the corrosion degree detecting method of the second embodiment of the invention.

FIGS. 7A and 7B are graphs showing the measuring conditions and measured results in the corrosion degree detecting method of the third embodiment of the invention.

FIGS. 8A and 8B are graphs showing the measuring results and measured results in the corrosion degree detecting method using a single pulse signal according to the third embodiment of the invention.

FIGS. 9A and 9B are graphs showing the measuring conditions and measured results in the corrosion degree detecting method using three pulse signals according to the third embodiment of the invention.

DESCRIPTION OF THE PREFERRED EMBODIMENT

Preferred embodiments of the invention will be described with reference to the drawings.

Embodiment 1

The first embodiment of the invention will be described. In this embodiment, materials being measured are SUS304 stainless steel that is formed by a solution-annealing of 1050° C., 30 min, and a heat-processed steel resulting from subjecting this steel to a sensitization process of 600° C., 24 hours. The sensitization degree corresponding to the intergranular corrosion resistance is measured for each of these materials. The former material is not sensitized and thus has a high intergranular corrosion resistance, while the latter sensitized material is greatly sensitized. The compositional difference between these materials is in the chromium concentration of the intergranular portion. The sensitized material has a low chromium concentration, and thus its intergranular portion has a low corrosion resistance, causing a stress corrosion crack (SCC) as well known so far in the corrosion tests. Therefore, all the embodiments which will be mentioned below use electrodes of these materials. Unless otherwise mentioned, the heat processing time for sensitizing is assumed to be 24 hours.

Figure 12:
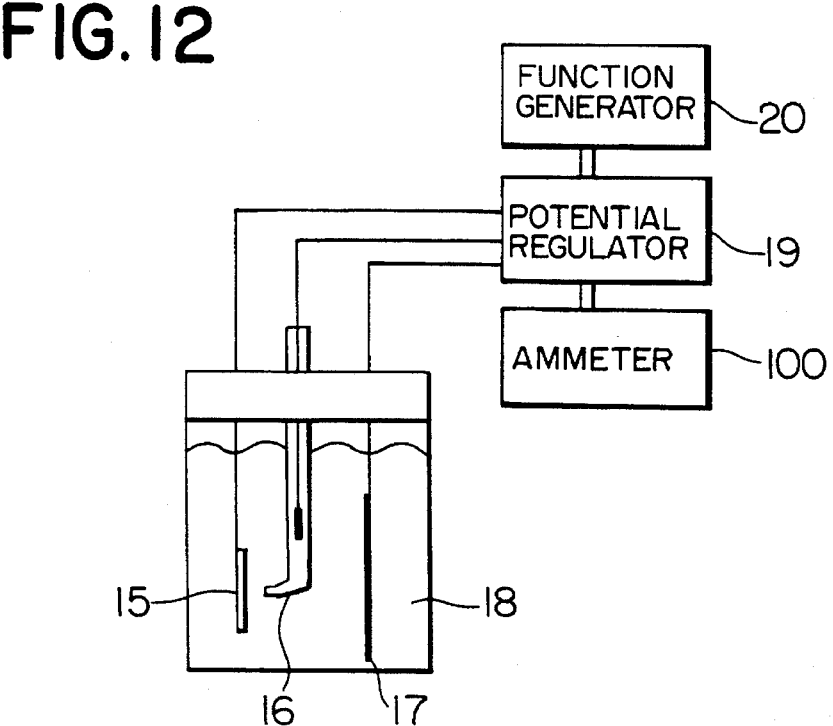
FIG. 12 is a block diagram of the construction of the measuring apparatus used in the first embodiment of the invention.

FIG. 12 shows a corrosion degree measuring apparatus of this embodiment. A sample electrode 15 is made of a material being measured. This sample electrode 15 is connected to a counter electrode 17 and a reference electrode 16, and these electrodes are immersed in an electrolytic solution 18 with which an electrolytic cell 26 is filled as shown in FIG. 12. In addition, the sample electrode 15, the counter electrode 17 and the reference electrode 16 are connected with a function generator 20 for generating a voltage signal shown in FIGS. 1B and 1C, a potential regulator 19 for regulating the voltage between the sample electrode 15 and the reference electrode 16 and supplying the pulse signal from the function generator 20 to these electrodes, and an ammeter 100 for measuring the magnitude of a current flowing between the sample electrode 15 and the counter electrode 17. The electrolytic solution 18 is a volume of 20 cm$^3$ of a 0.5-M $H_2SO_4$+0.01-M KSCN solution.

A method of measuring corrosion degree according to this embodiment will be described in detail. When the sample electrode 15 is immersed in the electrolytic solution 18, the natural potential is gradually decreased and, after a while, becomes constant, or about −0.2 V vs. SHE (hereinafter, the potential is expressed in the standard hydrogen electrode reference). A potential is momentarily applied to increase from this corrosion potential 6 to the passive state region, 0.450 V (hereinafter, referred to as the passive state potential) by the function generator 20 through a potentiostat and the potential regulator 19, and kept at this passive state potential for 60 seconds or above. The passive state potential of the material being measured is previously predicted or measured, and applied at the time of corrosion degree measurement. This potential is treated as the initial potential 1, and thereafter ten pulse signals are applied. At this time, the current response is measured by the ammeter 100. The pulse signal has a pulse width 2 of two seconds and an off-time 3 of five seconds, and a pulse height 4 (the peak potential 7 of the pulse) of the pulse signal is stepwise increased from 0.05 V by steps of a step-up potential 5 of 0.05 V. In this case, the current is sampled at the end of each pulse. FIGS. 1B and 1C show the waveform of the pulse signal according to this embodiment, and the current response at the time of applying the pulse signal. FIG. 1A shows a current-potential curve in which the abscissa indicates the peak potential of the pulse signal and the ordinate indicates the current response. In addition, a linear polarization curve is shown for comparison.

Figure 2:
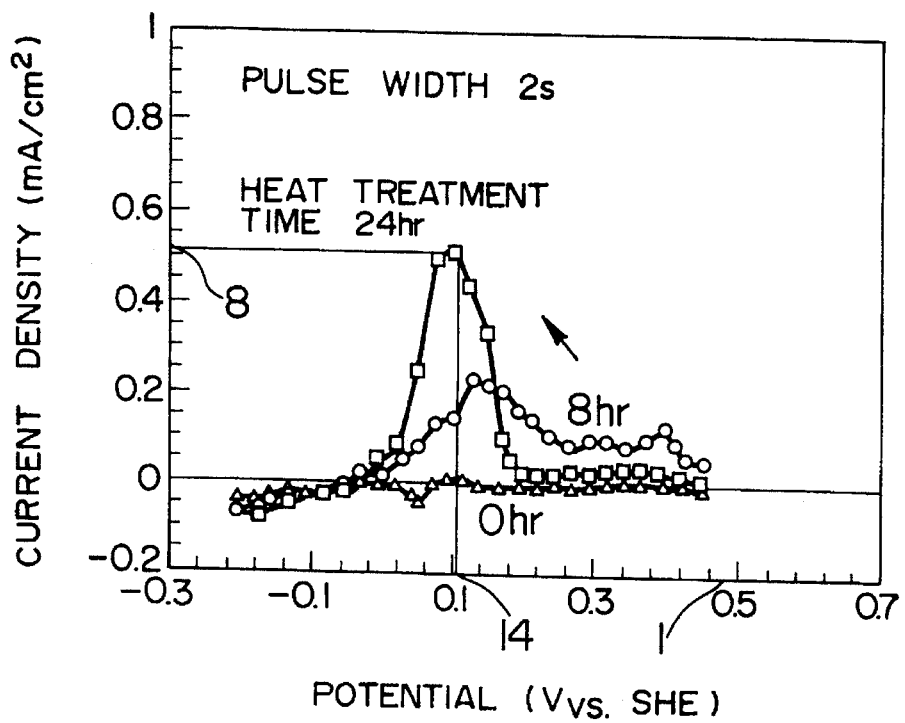
FIG. 2 is a graph showing the relation between the potential and response current density in the measuring method shown in FIG. 1.

FIG. 2 shows current density vs. potential curves for respective materials. The current in each material being measured (the solution-annealed materials, and the sensitized materials heated for 24 hours and 8 hours) is divided by the area of the sample electrode 15, to produce the current density. From FIG. 2 it will be seen that the sensitized materials have larger current densities than the solution-annealed ones. In addition, it was observed by use of an optical microscope that the sensitized material had selective corrosion in the intergranular portion while the solution-annealed one had a substantially uniform surface.

Therefore, the degree of the sensitization by heat treatment can be found from the current intensity which was measured by the corrosion degree measuring method of this embodiment. The current density of the sensitized materials, when the heat treatment time is variously changed, is increased with the increase of the heat treatment time, and becomes the maximum when the heat treatment time is about 48 hours. The solution-annealed material causes almost no current to flow. Thus, the degree of the sensitization can be known by comparing with the solution-annealed material.

In addition, the amount of current consumed and the measuring time per one sensitization degree measurement according to this method are 0.010 C/cm$^2$, and 1.7 min, respectively, or 1/1000 and 1/10 as much as 13 C/cm$^2$, and 15 min in the conventional EPR, respectively. Therefore, the amount of electrolysis in the sample electrode 15 is very small as compared with that in the prior art, and thus it does not contaminate the electrolytic solution, so that the corrosion degree can be measured with high precision.

Figure 3:
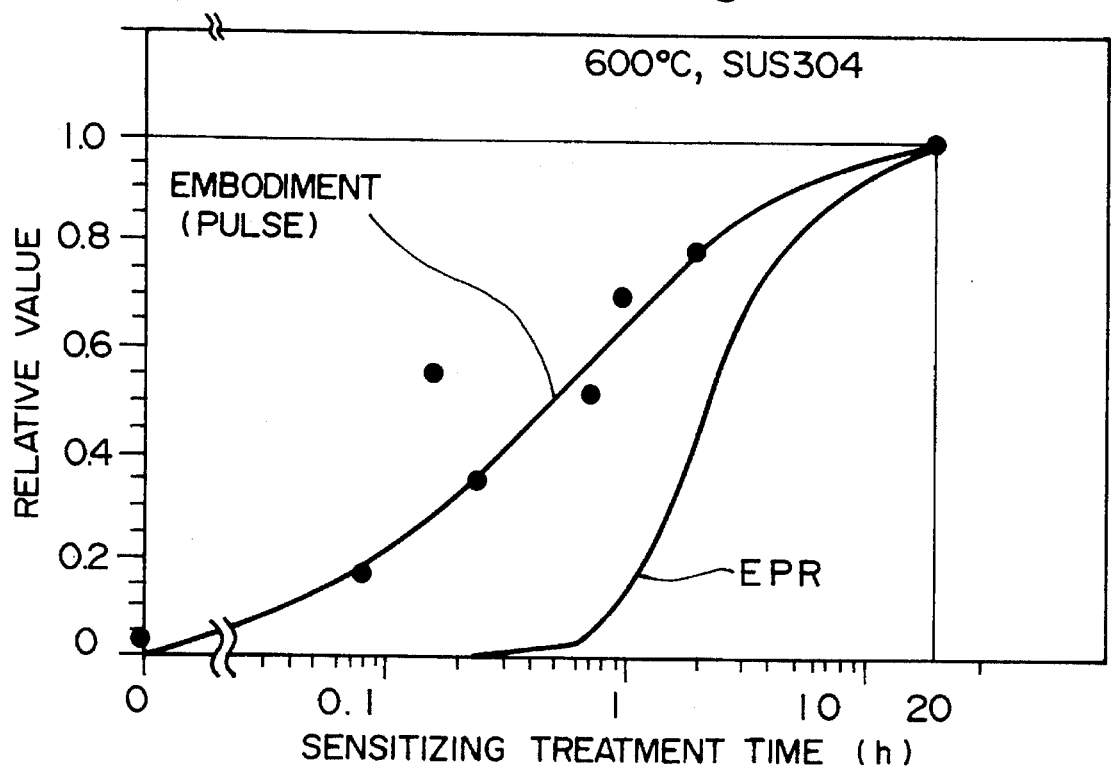
FIG. 3 is a graph showing the comparison between the measured result according to this invention and the measured result according to the prior art (EPR).

Moreover, from the current density vs. potential curves of FIG. 2, it will be seen that the current density has a peak 8 at around 0.1 V. This current density increases with the time for sensitization annealing. Therefore, the degree of sensitization can be measured by comparing the peak current densities. FIG. 3 shows the relative value of sensitization degree obtained from the magnitude of the peak current densities according to this embodiment and the relative value of sensitization degree obtained in the conventional EPR. In FIG. 3, the sensitization degree at the conditions of temperature 600° C. and heat treatment time 20 hours is assumed to be 1, and the relative value of sensitization degree is shown with respect to the heat treatment time. From FIG. 3 it will be seen that the EPR has a detection limit at a heat treatment time of 0.1 h while this embodiment can detect even at a shorter heat treatment time in which case the detection sensitivity is high.

Furthermore, from FIG. 2 it will be seen that a peak appears in the current density at substantially a constant potential irrespective of sensitization degree. For the sample electrode used in this embodiment, the peak appears at 0.1 V. Thus, as shown in FIG. 4, only a single pulse signal having the height 4 from the initial potential 1 to 0.1 V is applied and the current density is observed, thereby achieving the measurement of the sensitization degree in a short time and with a small amount of electricity.

Figure 15:
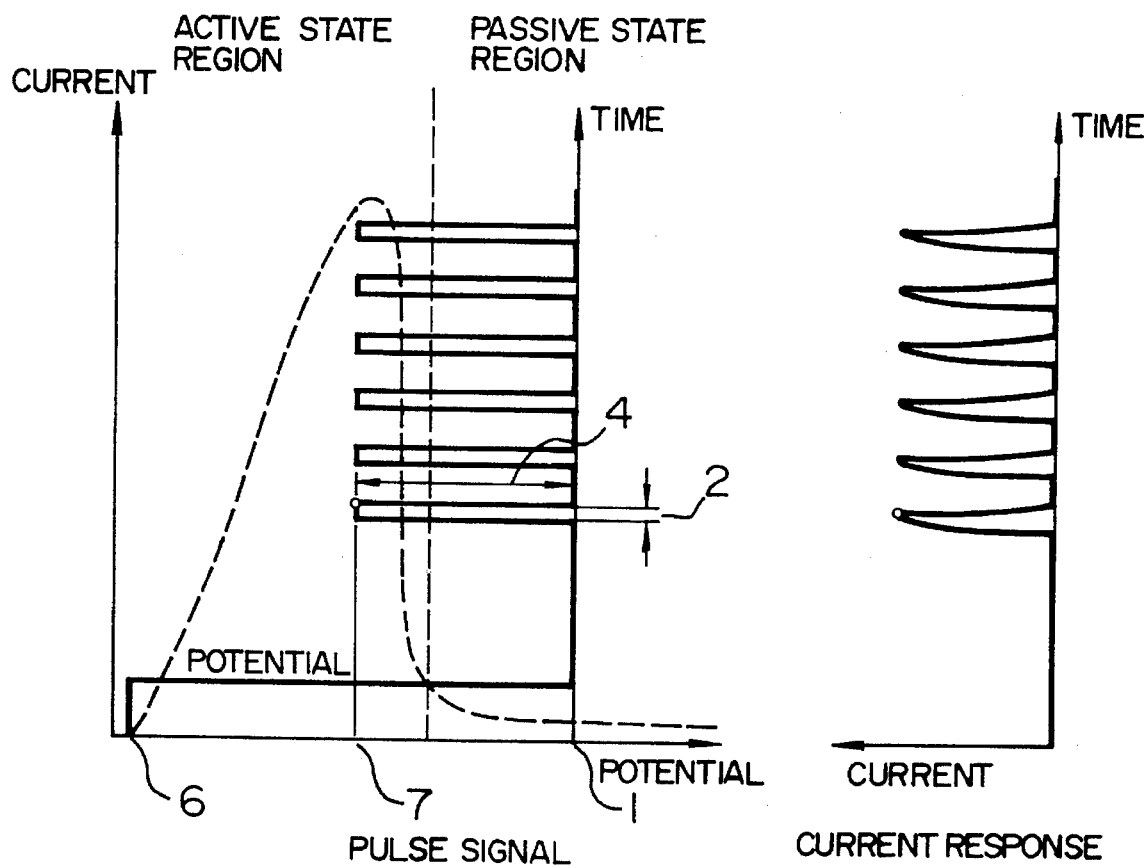
FIG. 15 is a graph showing the measuring conditions and measured results in the method of measuring the corrosion degree according to another embodiment of the invention.

As shown in FIG. 15, a plurality of pulses of an equal potential 7 are successively applied to a sample, and the maximum current value is selected from the values of currents flowing when a plurality of pulses are successively applied, or the total amount of electricity flowing when a plurality of pulses are successively applied is measured for each of samples and compared between the samples so that the sensitization degree can be determined. This method is effective for measuring the sensitization of the material in which, as in the material irradiated with neutrons, ions or the like, the chromium concentration is reduced at around the granular boundary so that the material is sensitized, and in which the Cr film on the bulk portion except around the granular boundary is relatively easy to be destroyed, although the bulk portion is not sensitized.

A description will be made of an example of the measurement of sensitization according to this method for the material SUS 316L irradiated with $1.0 \times 10^{19}$ helium ions/cm$^2$ at 500 degrees, and at an acceleration voltage of 300 keV and for the solution-annealed SUS 316L not irradiated.

In this measurement, the reference potential 1 was 0.450 V, the pulse potential 7 was 0.100 V, the pulse width 2 was 2 s, and the off-time time 3 was 5 s. The application of this pulse was repeated 100 times in succession. The pulse width 2 is determined so that the passive film on the intergranular portion of the irradiated material is completely destroyed and that the passive film on the bulk is not completely destroyed. The sensitization degree was evaluated from the total amount of electricity flowing when the pulse signal was applied.

The result was that the amount of electricity for the material not irradiated was evaluated to be about 0 C/cm$^2$, while the amount of electricity for the irradiated material was evaluated to be 0.05 C/cm$^2$. Therefore, it was found that this method is able to measure the sensitization degree. In addition, when the surfaces of the materials were observed by an optical microscope before and after the measurement, no change for the nonirradiated material was observed before and after the examination, but for the irradiated material a definite intergranular corrosion was observed on the intergranular portion and the dissolution of the bulk portion was not observed. Therefore, it was found that the amount of electricity of 0.05 C/cm$^2$ in the irradiated material includes information only about the sensitized intergranular portion.

Moreover, when the sensitization degree for these materials was measured by the conventional EPR method, a definite difference was observed between the reactivation rates of the irradiated material and nonirradiated material. However, it was found that the surfaces of both the intergranular portion and bulk portion on the irradiated material after examination were dissolved, and that the measured results included information on the dissolution of the non-sensitized portion. Thus, it was found that the measured result was evaluated to be larger than the true sensitization. On the other hand, according to the method of this embodiment shown in FIG. 15, since only the information about the sensitized intergranular portion can be measured, it is possible to precisely measure the sensitization due to the irradiation by which only around the intergranular portion is sensitized. In addition, by accumulatively measuring the total amount of electricity flowing when a plurality of pulses of the same potential are successively applied, it is possible to precisely measure the sensitization degree even though the amount of electricity flowing when each pulse is applied is very small.

Embodiment 2

Figure 6:
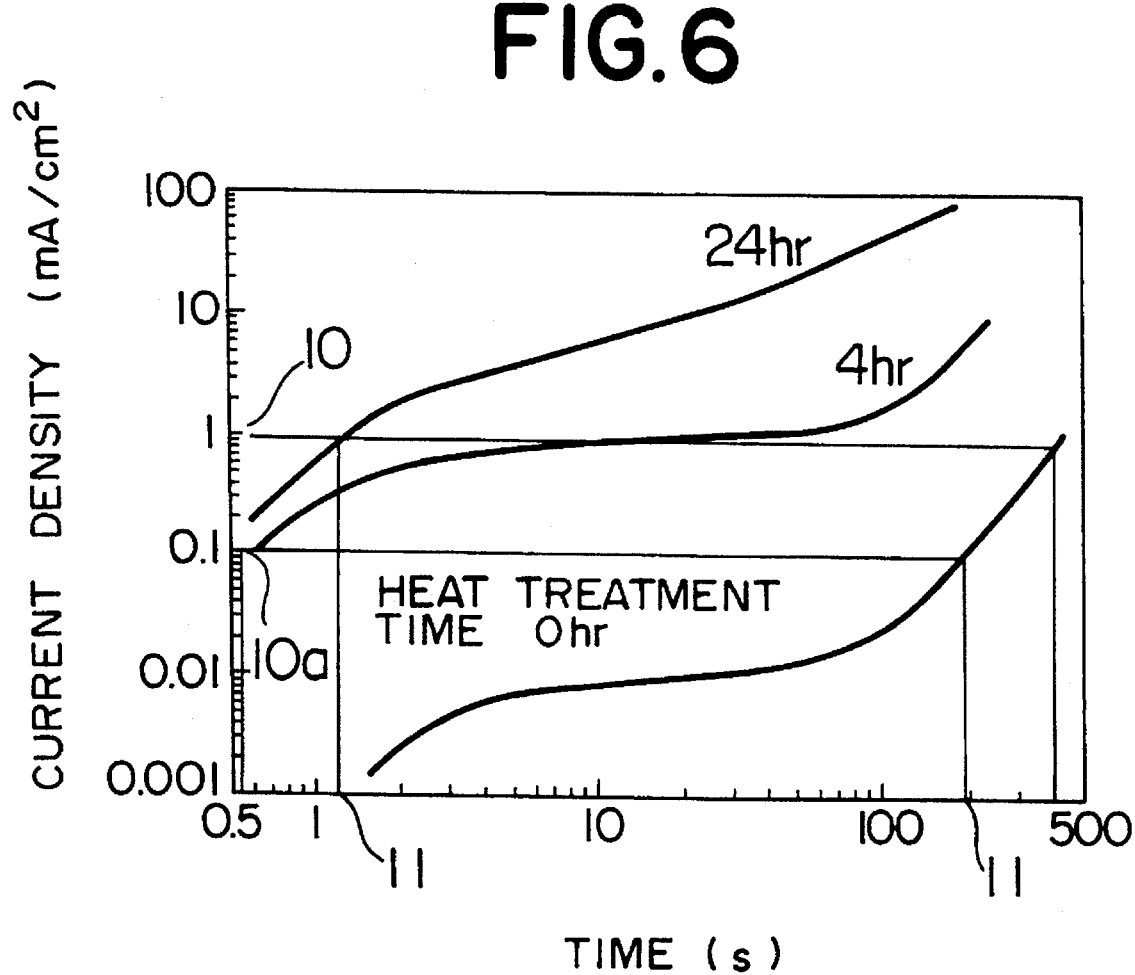
FIG. 6 is a graph showing the relation between time and response current density according to the measuring method shown in FIG. 5.

The corrosion degree measuring method of the second embodiment of the invention will be described below. The measurement apparatus is the same as in the first embodiment, and will not be described. In this embodiment, as shown in FIGS. 5A and 5B, a step signal of the initial potential 1 of the passive state region through the potential 9 is applied to the sample electrode 15, and the sensitization is measured from the time 11 in which the current density flowing in the sample electrode 15 and the counter electrode 17 reaches a set current density 10 (1 mA/cm$^2$). FIG. 6 shows the current response for the solution-annealed material and the sensitized material when a step signal of the initial potential 1 of 0.450 V through the step potential 9 of 0.100 V is applied. The corrosion degree measuring method of this embodiment considers the difference of current change with the passage of time between the solution-annealed material and the sensitized material. From FIG. 6 it will be seen that the current increase for the solution-annealed material is slower than that for the sensitized material. The time in which the current density reaches 1 mA/cm$^2$ after the stepwise change of potential is 400 s for the solution-annealed material and 1.1 s for the sensitized material, and thus a clear difference is recognized between these materials. Thus, the sensitization degree can be measured from the time in which a constant current density is reached.

After the electrode potential is stepwise changed from the initial potential 1 of 0.450 V to the step potential 7 of 0.100 V, the time is measured in which the density of current flowing between the sample electrode 15 and the counter electrode 17 reaches the set current density 10 of 0.1 mA/cm$^2$. As shown in FIG. 6, the time 11 in which the current density reaches the set value 10 is 200 s for the solution-annealed material and 0.55 s for the sensitized material. When the set current density is 1 mA/cm$^2$, the time necessary for the measurement completion tends to be too long. Conversely, when the set current density is 0.1 mA/cm$^2$ or below, the time resolution tends to be reduced in the strongly sensitized region. The highest sensitivity is obtained at a step potential of 0.100 V where a peak current is observed.

Embodiment 3

The third embodiment of the corrosion degree measuring method of the invention will be described below. The measuring apparatus is the same as in the embodiment 1 and thus will not be described. In this embodiment, the sensitization degree can be measured without knowing the electrode area. FIGS. 7A and 7B are graphs showing how to apply a pulse voltage signal according to this embodiment. When a pulse voltage signal beginning with the corrosion potential is applied in the anodic direction, the same current-potential curve is obtained for the solution-annealed material and sensitized material. Thus, the magnitude of the peak current appearing in the active region is also substantially constant irrespective of how to heat and processing time. Here, the peak current observed when the pulse signal is applied in the anodic direction is assumed to be a peak current 12 in the going direction. When the pulse voltage signal is applied from the passive state region in the cathodic direction as described in the embodiment 1, the magnitude of the peak current changes with the change of sensitization degree of materials. Here, the peak current density appearing when the pulse signal is applied in the cathodic direction is assumed to be a peak current 13 in the returning direction. Since the peak current density 12 in the going direction is substantially constant independently of the material used, the quotient of the returning peak current density 13 divided by the going peak current density 12 exhibits the sensitization degree of the material irrespective of the magnitude of the current between materials. Thus, the sensitization degree can be measured even if the area of each sample electrode is unknown.

When a pulse voltage signal having a pulse width of 0.1 s and an off time of 2 s was applied in the going direction, the peak current was 0.02 A for a sensitized material which was subjected to heat treatment for 24 hours and 0.01 A for another sensitized material which was subjected to heat treatment for one hour with their electrode area unknown. When a pulse voltage signal having a pulse width of 2 s and an off time of 5 s is applied in the returning direction, the peak current was 0.06 mA and 0.01 mA for those sensitized materials, respectively. The quotient of the returning peak current 12 divided by the going peak current was 0.003 and 0.001 for those materials, respectively. In order to confirm this method, the electrode area was measured, and the returning peak currents 13 for those materials were converted into current densities, 0.6 mA/cm$^2$ and 0.2 mA/cm$^2$, respectively. From the comparison of both methods, it was confirmed that the ratio between the heat treatment times 24 h and 1 h was 3/1 for both methods and that this method can detect the sensitization degree without measuring the electrode area.

According to this embodiment, since the potential at which a peak appears is substantially constant irrespective of the sensitization degree for materials, a pulse signal having a pulse height, or potential at which one peak appears is applied in both going and returning direction as shown in FIGS. 8A and 8B, and the sensitization degree is determined from the magnitudes of the currents in the same way as in the embodiment 7. Since the pulse signal is applied once for each direction, the measurement time and amount of electricity can be reduced.

Figures 10A, 10B:
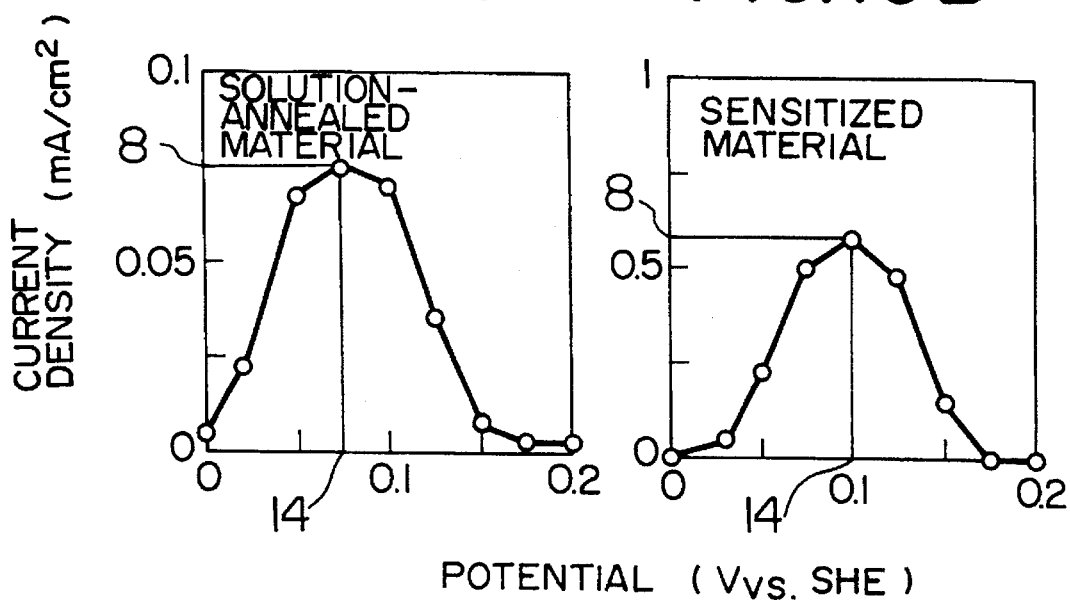
FIGS. 10A and 10B are graphs showing the measured results according to the method shown in FIG. 9.

The measurement according this embodiment sometimes detects the shift of the potential at which a peak current appears because the materials used have different chemical compositions and because the solution has a resistance to current. If this phenomenon cannot be predicted, it is not possible to measure the magnitudes of peak currents which are produced when a pulse signal is applied in the going and returning directions as described above. In order to avoid this, two or more pulse voltage signals having potentials around the peak may be applied. FIGS. 9A and 9B are conceptual diagrams showing this idea. FIGS. 10A and 10B are graphs showing current-potential curves for the solution-annealed material and sensitized material which were observed when a pulse voltage signal of a step up voltage 0.025 V which has an initial potential of 0.450 V, a pulse width of 2 s and an off time 5 s is applied to give potentials ranging from 0.200 V to 0 V. The peak current densities for the solution-annealed material and sensitized material which can be derived from those curves are 0.02 mA/cm$^2$ for 0.075 V and 0.6 mA/cm$^2$ for 0.100 V. Even if the potential at which a peak current appears is shifted, this method can correctly detect the sensitization. In addition, this method can be used when the pulse signal is applied in the master direction so that the peak current is determined as in the embodiment 7. The current-potential curves measured according to this method are shown in FIGS. 10A and 10B. As shown in FIGS. 10A and 10B, the solution-annealed material has the smallest current density, or has a low sensitization degree. Thus, the degree of sensitization can be known by comparing with this.

Embodiment 4

Figures 11A, 11B:
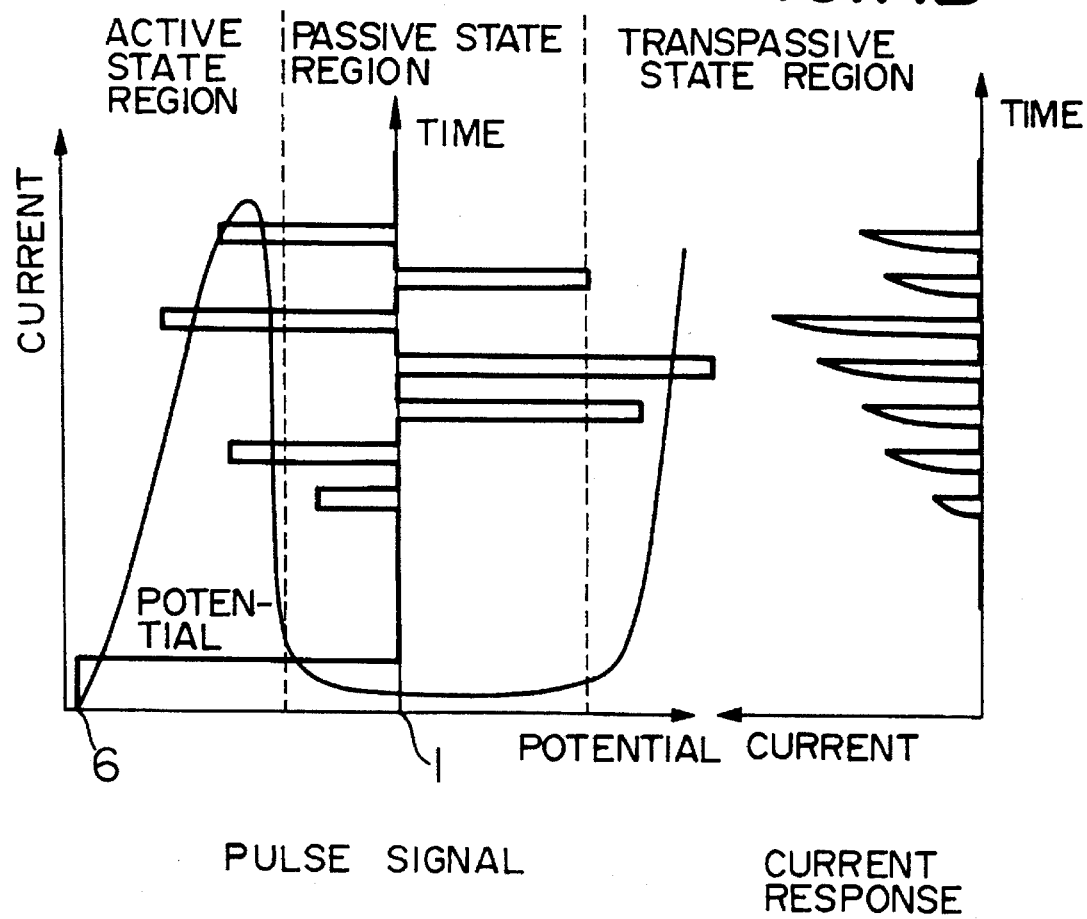
FIGS. 11A and 11B are graphs showing the measuring conditions and measured results in the corrosion degree detecting method using a single pulse signal according to the fourth embodiment of the invention.

The fourth embodiment of this invention will be described. FIGS. 11A and 11B show a scheme for continuously determining both the sensitization degree and the intergranular corrosion resistance at around the transpassive state starting potential. Two pulse voltage signals having an initial potential 1 of 0.450 V, a pulse width of 2 s and peak potentials of 0.100 V corresponding to the active region and 1.100 V corresponding to the transpassive state region are applied to the solution-annealed material and the sensitized material. The current density in the solution-annealed material at the potential of 0.100 V was 0.075 mA/cm$^2$, and the current density at 1.100 V was 5 mA/cm$^2$. The corresponding current densities of the solution-annealed material were 0.6 mA/cm$^2$ and 3 mA/cm$^2$, and thus they are large in the active region and transpassive state region, or the intergranular corrosion resistance is small. In addition, the order in which the pulse signal is applied in the anodic or cathodic direction may be arbitrary, and the pulse height may be random.

An experiment was made for confirming the relation between the current value and the intergranular corrosion resistance when a pulse voltage corresponding to the transpassive state region is applied. When a pulse signal was applied in the anodic direction from the initial potential corresponding to the passive state region to a SUS304 stainless steel and to another SUS304 stainless steel containing 0.07 wt % of boron about two figures more than normal with both materials immersed in the nitric acid solution, the current values were measured for those materials. The transpassive state starting potential of the stainless steel containing boron was on the cathodic side relative to the normal stainless steel. Also, the current value in the stainless steel containing boron was larger than that in the normal stainless steel at the same potential. In general, it is known that the intergranular corrosion resistance in the transpassive state region is reduced by the addition of boron. Thus, it was confirmed that the intergranular corrosion characteristic can be known from the current value to the pulse signal or the transpassive state starting potential.

Embodiment 5

In the electrochemical scan type tunnel microscope, if a pulse signal generator is incorporated in the voltage supply source for applying a voltage between the probe tip and the sample, the pulse signal can be applied to the sample electrode counter to the reference electrode. When the pulse signal is applied the instant that the tip is scanned to obtain a surface image with the sample electrode kept in the passive state or each time one-surface canning is made, the corrosion momentarily progresses. When this operation is continuously repeated, the tunnel microscope image is changed, and the changing region corresponds to the corrosion site. Since the rate of change indicates the corrosion degree of metal, the amount of local corrosion can be measured. The present electrochemical scan type tunnel microscope is able to scan a maximum range of 0.1× 0.1 mm. The frequency of corrosion generation is sometimes high over this region, and hence it will become difficult to detect the corrosion within this narrow range. Therefore, the scanning vibrating electrode technique is used which can scan a larger range than the electrochemical scan type tunnel microscope. In this case, the principle on which the pulse voltage is applied, and the effect are the same as in the above embodiments.

The corrosion degree measuring methods of the embodiments 1, 2, 3 and 4 can be used to evaluate the defects and characteristics of the nonconductive film which was formed on a metal material by CVD, PVD, ion mixing, sputtering, ion plating or vapor deposition. If the nonconductive film formed on a metal material is imperfect, the metal, or bulk material gets wet with the electrolytic solution in which this metal material with the nonconductive film is immersed. At this time, if a pulse signal is applied to the metal material, a current flows in accordance with the area over which the metal is wet with the solution, or the extent at which the film covers the metal surface. Thus, the corrosion resistance and film functions of the film-formed metal material can be evaluated from the magnitude of the current. Since the pulse signal is applied to flow a small current and in a short period, the material is not dissolved or destroyed by this pulse signal.

The corrosion degree measuring methods of the embodiments 1, 2, 3 and 4 are also used to evaluate the metal thin film formed on the surface of the crystal resonator. The crystal resonator with a metal thin film formed on the surface is immersed in an electrolytic solution while it is operated to vibrate, and a pulse signal is applied to the resonator. The corrosion degree of metal is measured from the change of the oscillation frequency of the crystal resonator. This method is the application of QCM and SAW device methods in order to measure the corrosion resistance of the film. When the thin film formed on the crystal resonator is increased or decreased in its weight by corrosion or the like, the oscillation frequency of the crystal resonator changes in accordance with the change of the weight. The corrosion resistance of the thin film, when the pulse signal is applied to the electrode immersed in the electrolytic solution, is evaluated from the change of the oscillation frequency. In the above embodiments 1, 2, 3 and 4, the potential at which a returning peak current appears independently of the heat treatment time and temperature for sensitization was 0.100± 0.050 V.

In the embodiments 1, 2, 3 and 4, when the sensitization degree was measured at an initial potential on the cathodic side relative to 0.4 V, the reproducibility was poor. After a measurement according to the method of embodiment 3 was repeated several times with an initial potential of 0.300 V applied to a sensitized material, the tenth measured value was 70% of the first measured value. On the other hand, when the initial potential was changed to 0.450 V, it fell within 90%. Since this reproducibility is suddenly reduced when the initial potential is smaller than 0.4 V, the initial potential is desirably set to be larger than 0.4 V. However, the initial potential must not exceed the passive state region.

In the measuring apparatus of the embodiment 2, when a coulomb meter was used in place of the ammeter 100 to measure a melt-processed material and a sensitized material, the measured values for these materials were 0.15 mC/cm$^2$ and 1.1 mC/cm$^2$. Thus, the electric quantity indicates the sensitization degree as well as the current density.

In the embodiments 1, 2, 3 and 4, the voltage signal of which the pulse width is larger than five seconds will suddenly increase the quantity of electricity, but the voltage signal of which the pulse width is less than one second cannot clearly discriminate the characteristics between the materials. Therefore, the voltage signal should have a pulse width ranging from one second to five seconds.

In the embodiments 1, 2, 3 and 4, when the potential of the sample electrode 15 is stepwise changed from the corrosion potential to the passive state region, a constant time, or 60 seconds is necessary for the passive film to be stabilized until the measurement is started. If the measurement of embodiment 2 is started 30 seconds after the passive state, the peak current density for the solution-annealed material is 0.2 mA/cm$^2$, or about 2.5 times as large as when the measurement is started 60 seconds thereafter. Thus, the sensitization degree cannot be correctly detected.

The passive state maintaining current density after 60 seconds sometimes changes depending on the material and extent of sensitization. In this case, in order for the passive film of each sample electrode to be kept in the same state, the pulse signal is started to apply when the passive state maintaining current density is reduced to 0.05 mA/cm$^2$. When the current density is less than 0.05 mA/cm$^2$, the reproducibility becomes satisfactory.

In the embodiments 1, 2, 3 and 4, while a sulfuric acid+ potassium thiocyanate solution was used as the electrolytic solution 18, another electrolytic solution for the same measurement may be used which contains any one of nitric acid, hydrochloric aid, perchloric acid, hypochlorous acid, acetic acid, cyanic acid, salts thereof, carbonate, ammonium, ammonium salt, and hydroxide of metal.

In the embodiments 1, 2, 3 and 4, while the potential including a corrosion potential 6 through a predetermined passive state potential (initial potential 1) is momentarily applied to the electrode, this embodiment is not limited to this way of potential application, but may gradually apply the potential by use of the linear polarization method. In this case, the amount of electrolysis in the sample electrode 15 increases as compared with the case in which the potential of up to the passive state potential (initial potential 1) is momentarily applied. However, the amount of electrolysis is decreased by two figures or above as compared with the conventional EPR in which the quantity of the solution is decreased, and thus the precision in the corrosion degree measurement is not reduced. When the passive state potential of the material being measured cannot be previously predicted or measured, the linear polarization method may be used by which the passive state potential can be determined while the current at the time of corrosion degree measurement is being detected.

Embodiment 6

Figure 13:
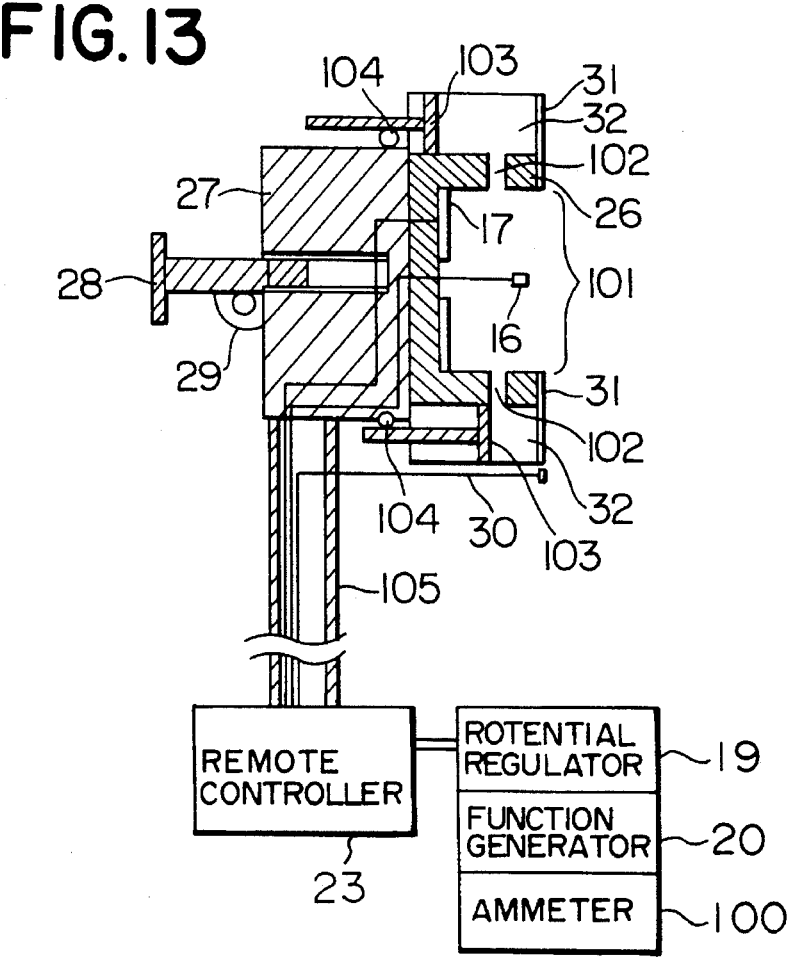
FIG. 13 is a block diagram of the construction of the remote-controlled type measuring apparatus for corrosion degree which is used in the fifth embodiment of the invention.

The measuring apparatus of the sixth embodiment of the invention will be described. FIG. 13 is a diagram of a remote-control type corrosion degree measuring apparatus for measuring, in the field, the intergranular corrosion degree of the material of which a plant is made. In this embodiment, the inner wall of a hollow pipe which is made of a metal material is used as the sample electrode 15 and the corrosion degree of the inner wall at the middle point is measured by use of this measuring apparatus. There is shown an electrochemical cell 26, which has an opening 101 through which the electrolytic solution is made in contact with the inner wall of the hollow pipe, and two inlets 102 through which the electrolytic solution is injected into the cell. This cell has a capacity of 0.2 cm$^3$. The opening 101 is formed to have a shape conforming with the inner wall of the hollow pipe being measured. A solution-leaking prevention seal 31 is mounted around the opening 101 of the electrochemical cell 26. Solution cylinders 32 for holding the electrolytic solution are respectively connected to the two injection inlets 102 of the electrochemical cell 26. Each of the solution cylinders 32 has a motor 104 for driving a piston 103 in response to the command from a remote controller 23. In addition, a supporting member 27 is connected to the surface of the electrochemical cell 26 which opposes to the opening 101. This supporting member 27 has a stretchable fixing bar 28 and a motor 29 for driving the fixing bar to expand and contract in response to the command from the remote controller 23.

The electrochemical cell 26 also has the reference electrode 16 and the counter electrode 17 mounted therein. These electrodes are fixed to the supporting member 27. A structural material contact terminal 30 for being made in contact with the inner wall of the hollow pipe being measured is mounted around the opening 101. The contact terminal 30 is electrically connected to the counter electrode 17 and the reference electrode 16. A hollow supporting bar 105 is fixed to the supporting member 27. The one ends of the leads the other ends of which are connected to the contact terminal 30, the counter electrode 17 and the reference electrode 16 are passed through the hollow supporting bar 105 and connected to the remote controller 23. The remote controller 23 is connected to the potential regulator 19, the function generator 20 and the ammeter 100. The potential of the inner wall of the hollow pipe is controlled relative to the reference electrode 16 by the potential regulator 19. The pulse signal for the corrosion degree measurement mentioned in the above embodiments is generated from the function generator 20. The current flowing between the inner wall of the hollow pipe and the counter electrode 17 is measured by the ammeter 100.

Figure 14:
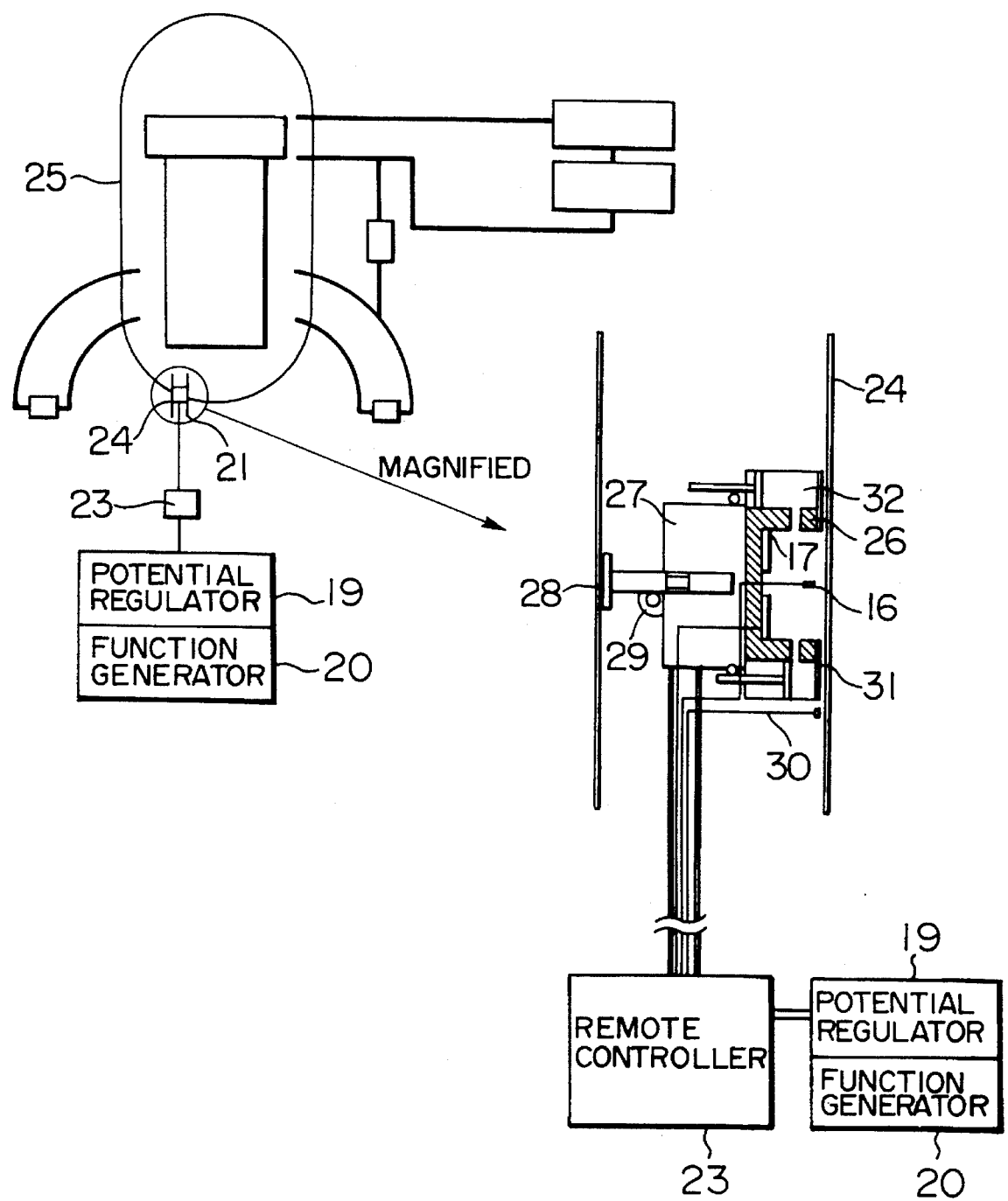
FIG. 14 is an explanatory diagram showing the remote-controlled type corrosion degree measuring apparatus of FIG. 13 for measuring the sensitization of the ICM housing portion of a nuclear power pressure vessel.

This measuring apparatus was used to measure the sensitization degree of the ICM housing portion (hollow pipe) in a simulated nuclear power plant which had been operated for fifteen years. FIG. 14 shows the application of this measuring apparatus to the simulated nuclear power pressure vessel. The electrochemical cell 26 for remote-controlled type corrosion degree measurement was remote-controlled to be brought to the inner wall of the ICM housing by the supporting bar 105. Then, the fixing bar 28 was drawn out and fixed by the remote control so that the opening 101 of the electrochemical cell 26 could be made in close contact with the inner wall of the pipe. The piston 103 was operated to compress the solution cylinder 32, thereby filling the electrolytic solution within the electrochemical cell 26.

Thereafter, the measuring method mentioned in the above embodiments 1, 2, 3 and 4 was used to measure the corrosion degree of the inner wall. After the measurement, the piston 103 was driven to absorb the solution up and feed it to the solution cylinder 32, and the fixing bar 28 was contracted so that the electrochemical cell 26 could be taken out of the inner surface of the ICM housing.

The result of the measurement using the method of the embodiment 2 was that the peak current for the material of the housing was 0.05 mA/cm$^2$ which is substantially the same as that for the reference sample allowing for safety. The peak current for the strongly sensitized one of the same material was 0.8 mA/cm$^2$. Accordingly, it was confirmed that the ICM housing portion was maintained in good condition.

According to this embodiment, since the methods of the embodiments 1, 2, 3 and 4 can be used, the amount of electricity necessary for the measurement is less than 1/1000 as low as that in the conventional EPR method, and thus the amount of the electrolytic solution may be 0.2 cm$^3$, or 1/1000 that in the conventional method. Therefore, since the capacity of the electrochemical cell 26 is very small, or 0.2 cm$^3$, the measuring apparatus can be small-sized. By this measuring apparatus, it is possible to measure the corrosion degree for the inner wall surface of even a narrow pipe. In addition, since the measuring time is short, the time during which the plant is stopped for the field measurement of the corrosion degree can be decreased.

The corrosion degree measuring method of each embodiment mentioned above considers the fact that the easiness with which the passive film is broken changes depending on the composition of materials and the sensitization of the structure. In addition to the measurement of sensitization degree, this method may be applied to the measurement for the intergranular corrosion resistance around the transpassive state starting potential, and the hall-or gap-corrosion resistance in a chloride solution or for the electrochemical examination of the characteristics of the passive film concerning the corrosion resistance.

The corrosion degree measuring method and apparatus of each embodiment mentioned above have the following three effects as compared with the prior method technique: 1. the reduction of the amount of electricity for measurement, 2. the reduction of the measuring time, and 3. the increase of the detection sensitivity. Thus, it is possible to not only evaluate at a high efficiency and at a high precision the intergranular corrosion characteristics of materials in the laboratory level, but also measure the intergranular corrosion of the plant's structural materials, particularly the field measurement of the sensitization degree, in the place where persons cannot enter and is difficult to measure, or suffer from radiation, and in a narrow space. The field measurement in such a place will need a remote controller. According to the embodiments, since the amount of electricity necessary for measurement is less than 1/1000 that in the prior art, the capacity for the test solution can be reduced to 0.2 cm$^3$ or below from the principle point of view. Thus, it is not necessary to exchange the electrolytic solution, and the measuring structure to be remotely controlled can be small-sized and simplified. In addition, since the measuring time is short, a plurality of places are easy to measure. Moreover, since the detection sensitivity is high, it will be possible to detect the sensitization phenomenon due to radiation which was difficult to detect in the prior art. Accordingly, the life spans of a variety of plants can be promptly known, and the reliability of plants can be maintained high on the basis of the confirmation of good or bad condition after the repair work and the plans for the maintenance and examination.

Embodiment 7

Figure 16:
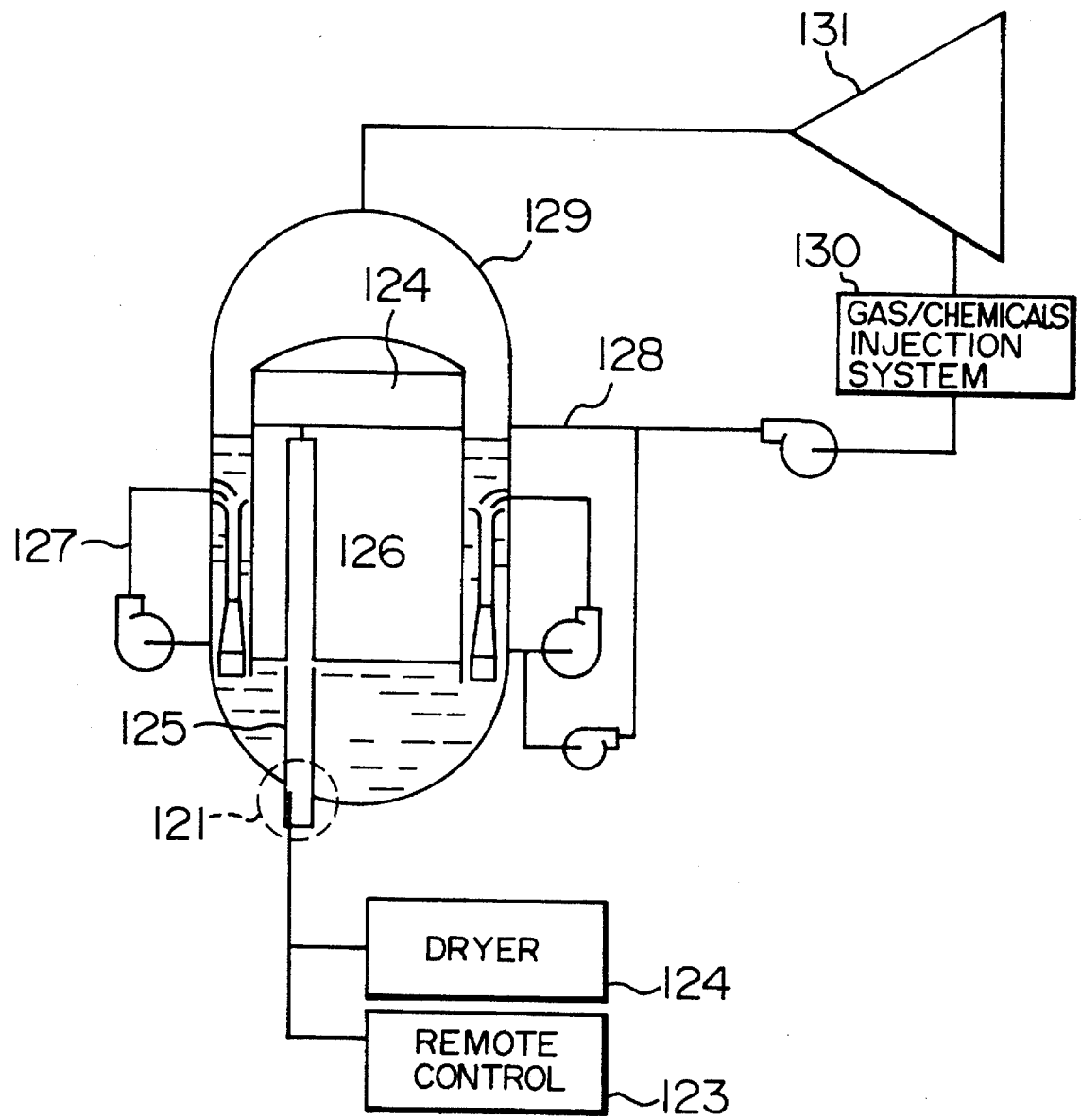
FIG. 16 is a schematic diagram of the sensitization detecting system of the invention used in the ICM housing of a nuclear reactor.

FIG. 16 shows one example of the application of the invention to a BWR nuclear plant. The very small electrochemical cell shown in FIG. 13 is inserted into an ICM housing 121 shown in FIG. 16, and it is connected to a pulse electrochemical measuring system 120, and to a remote control system 123 for the very small electrochemical cell. Shown at 124 is a dryer, 125 is an inter-furnace measuring pipe, 126 is a furnace center, 127 is a nuclear reactor recirculation system, 128 is a nuclear reactor water supply pipe, 129 is a nuclear pressure container, 130 is a gas/chemicals injection system, and 131 is a turbine.

Figure 17:
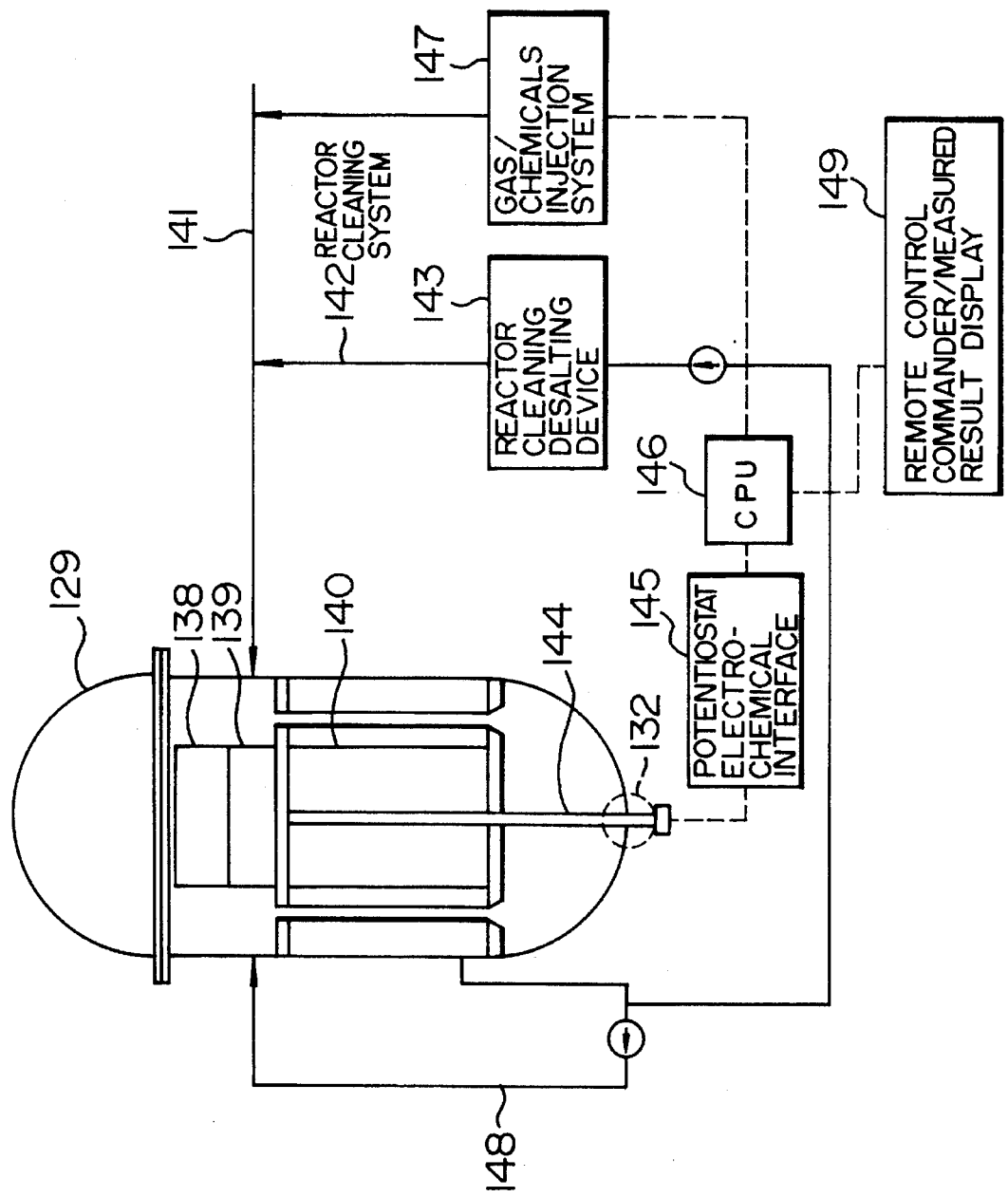
FIG. 17 is a schematic diagram of the water quality control system of the invention, for a BWR plant having a three-electrode system within the measuring pipe of a nuclear reactor.
Figure 18:
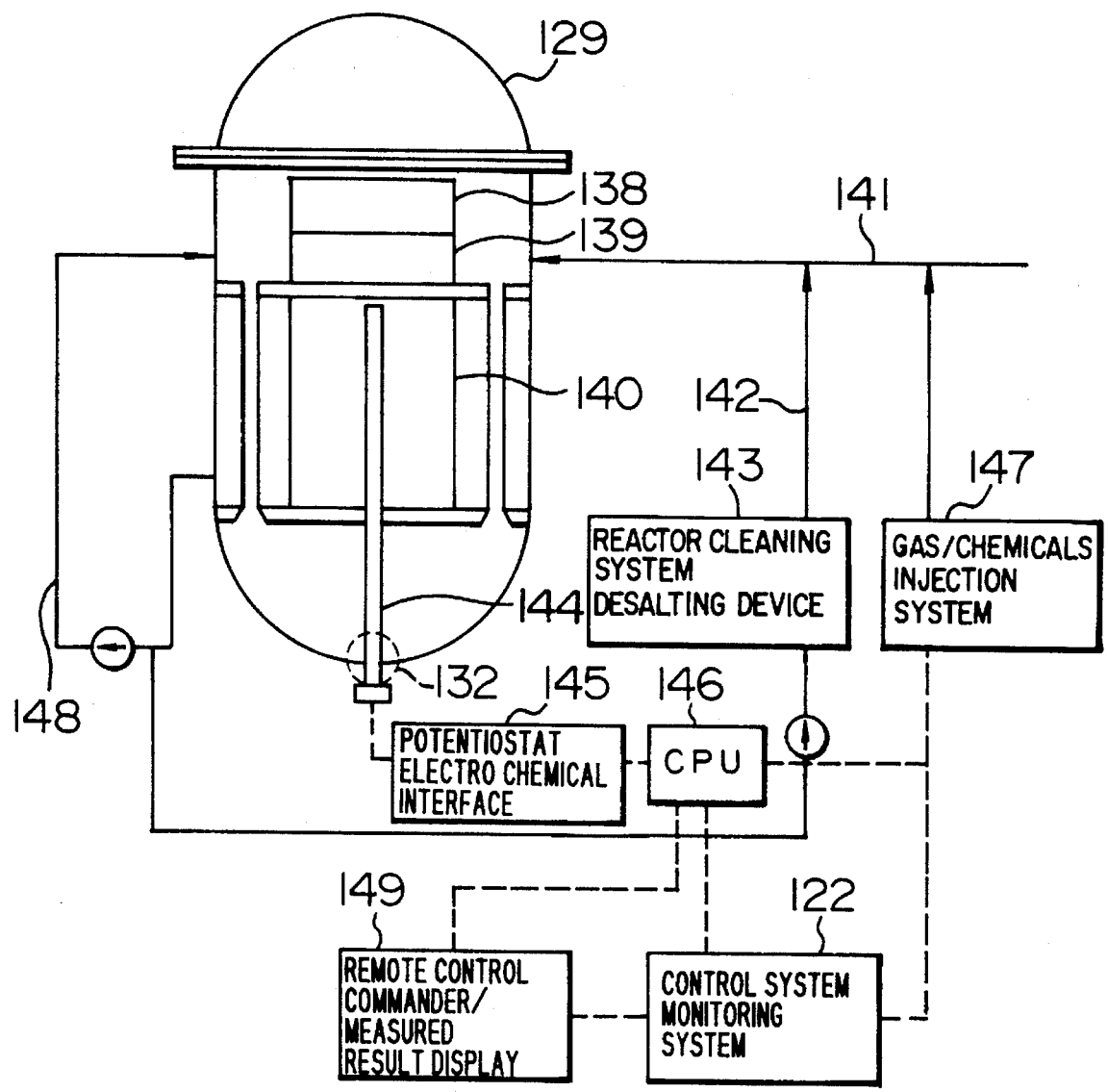
FIG. 18 is a schematic diagram of the safety diagnosis control system of the invention used in a nuclear reactor.

FIGS. 17 and 18 show particularly the location and construction of the three-electrode system within the BWR nuclear reactor pressure container of the BWR nuclear, and the principle of a sensitization degree measuring system, water quality control system and stability diagnosis system.

FIG. 17 shows the peripheral elements of the BWR nuclear pressure container 129. The electrode housing is the same as in the embodiment 1. The three-electrode system electrode housing 132 is inserted into an inter-furnace measuring pipe 144, and provided in the furnace center 140. Also, there are shown the nuclear reactor pressure container 129, the electrode housing 132, a counter electrode 133, a reference electrode 135, an electrode support 136, a neutron measuring pipe 137, a dryer 138, a separator 139, the furnace center 140, a nuclear reactor water supply pipe 141, a nuclear reactor cleaning system 142, a nuclear reactor cleaning desalting device 143, an inter-furnace measuring pipe 144, a potentiostat electrochemical interface 145, a CPU 146, a gas/chemicals injection system 147, a nuclear reactor recirculation pipe 148, and a remote control commander/measured result display 149. The monitor electrode 134 is actuated by the potentiostat, electrochemical interface 145 and the CPU (computer arithmetic unit and automatic controller) 146. The measured result is fed to the remote control commander/measured result display 149.

The measured result is compared with the previously fed reference value within the CPU 146, and the water quality control parameter at the time of operation is determined on the basis of the compared result. Upon start of operation, the CPU 146 sends a command to the control system of the gas/chemicals injecting system 147, opening or closing the feed valve, and this operation is repeated to control the quality of water.

The reference electrode 135 may be a saturation calomel electrode (SCE), standard hydrogen electrode (SHE), silver-silver chloride electrode (AgAgCl) or the like. The broken line indicates the connection of an electric circuit, interface bus line and so on.

The electrodes can be provided, as is the inter-furnace measuring pipe, at the dryer 138, the separator 139, the radiation test piece inserting jig or other drawable apparatus and parts, and placed within the nuclear reactor pressure container. It can also be directly placed on the wall of the pressure container.

FIG. 18 shows the addition of the control monitoring system 122 for monitoring the water quality control system to the BWR nuclear reactor including the electrodes and electrolytic cell used in FIG. 16. The control monitoring system 122 has at least one computer arithmetic unit which decides whether the CPU 146 for controlling the water quality control system and the electrochemical interface 145 are correctly operated or not, thereby keeping the high reliability and stability of the water quality control system. The diagnosis for the detection of abnormal operations is performed by connecting the water quality control system formed of the electrochemical interface 145, CPU 146 and gas/chemicals injection system 147 to the dummy circuit and deciding whether or not the calculated results, measured results and control results lie within predetermined allowable ranges.

These measurement processes are made within the potentiostat/electrochemical interface 145 and CPU (computer arithmetic unit, automatic controller) 146, and the measured results are compared with reference values. The gas/chemical injection system 147 is controlled by the compared results, thereby controlling the water quality.

According to this embodiment, since the electrochemical cell can be small-sized and since the sensitization degree of the material of which the plant is made can be detected and evaluated in a short time by remote control, it is possible to detect the sensitization degree within a narrow, small pipe, which cannot be detected by the prior art. Thus, the present condition, health of the material of which the plant is made can be widely and quickly known, with the result that the operation of the plant can be maintained at a high level.

According to the corrosion degree measuring method of the invention, it is possible to measure the intergranular corrosion of the plant's structural materials in a narrow space, particularly make the field measurement of the sensitization degree.

We claim:

1. A method of measuring the corrosion degree of a material being measured by immersing a metal electrode made of said material being measured and a counter electrode disposed so as to face said metal electrode in an electrolytic solution, applying a voltage to said metal electrode, measuring a current flowing between said metal electrode and said counter electrode, and determining the corrosion degree of said material being measured, comprising the steps of:

applying a voltage changing in an anodic direction to said metal electrode which said metal electrode is at an initial potential when said metal electrode is immersed in said electrolytic solution, so that the potential of said metal electrode is raised from said initial potential which is a corrosion potential up to a passive state potential at which said metal electrode made of said material being measured reaches a passive state region, and is kept at said passive state potential; and applying a pulse voltage signal in a cathodic direction with respect to a reference potential to said metal electrode which is kept at said passive state potential as said reference potential, measuring the intensity of a current flowing between said metal electrode and said counter electrode at the time of said pulse voltage application, and determining the corrosion degree of said material being measured from said current intensity.

2. A method of measuring the corrosion degree of a material being measured according to claim 1, wherein at the time of said voltage application for said passive state potential the potential of said metal electrode is momentarily raised up to said passive state potential for said material.

3. A method of measuring the corrosion degree of a material being measured according to claim 1, wherein the cathodic peak potential of said pulse voltage signal in said cathodic direction lies between said initial potential and said passive state potential, and said cathodic peak potential is high enough to break the passive state film on said metal electrode.

4. A method of measuring the corrosion degree of a material being measured according to claim 3, wherein said pulse voltage signal changing in said cathodic direction is formed of a plurality of pulse voltage signals of different peak potentials, which are applied in order, and the largest one of the current values measured when said plurality of pulse voltage signals are applied is selected and used for determining the corrosion degree.

5. A method of measuring the corrosion degree of a material being measured according to claim 3, wherein said pulse voltage signal changing in said cathodic direction is formed of a single pulse voltage signal having a predetermined peak potential.

6. A method of measuring the corrosion degree of a material being measured according to claim 4 or 5, wherein the measured magnitude of said current is divided by the surface area of said metal electrode so that a current density is found, and the corrosion degree of said material is determined from said current density.

7. A method of measuring the corrosion degree of a material being measured according to claim 6, wherein said current density calculated for said material and said current density previously obtained for a reference material having a known sensitization degree are compared with each other so as to find the sensitization degree of said material being measured.

8. A method of measuring the corrosion degree of a material being measured according to claim 7, wherein said reference material is a solution-annealed material.

9. A method of measuring the corrosion degree of a material being measured according to claim 4 or 5, wherein a pulse voltage signal which changes in an anodic direction and of which the peak potential lies between said initial potential and said passive state potential is applied to said metal electrode which is kept at said initial potential as a reference potential, the intensity of a current is measured which flows between said metal electrode and said counter electrode at the time of said pulse voltage application, the ratio between said intensity of said current flowing when said voltage signal changing in said anodic direction is applied and said intensity of said current flowing when said voltage signal changing in said cathodic direction is applied is calculated, and then the corrosion degree is determined from said ratio.

10. A method of measuring the corrosion degree of a material being measured according to claim 9, wherein said pulse voltage signal changing in said anodic direction is formed of a plurality of pulse voltage signals of different peak potentials which are applied, and the largest one of said current values measured when said plurality of pulse voltage signals are applied is selected and used for determining the corrosion degree.

11. A method of measuring the corrosion degree of a material being measured according to claim 9, wherein said pulse voltage signal changing in said anodic direction is formed of a single pulse voltage signal having a predetermined peak potential.

12. A method of measuring the corrosion degree of a material being measured according to claim 9, wherein said ratio calculated for said material being measured and said ratio calculated for a reference material having a known sensitization degree are compared with each other to determine the sensitization degree of said material being measured.

13. A method of measuring the corrosion degree of a material being measured according to claim 1, wherein an amount of electricity is determined from said current value and the corrosion degree is determined from said amount of electricity.

14. A method of measuring the corrosion degree of a material being measured according to claim 1, wherein after the potential of said metal electrode is raised up to said passive state potential, it is kept at said passive state potential for at least 60 seconds until said pulse voltage signal is applied.

15. A method of measuring the corrosion degree of a material being measured according to claim 1, wherein after the potential of said metal electrode is raised up to said passive state potential, the current density for keeping said metal electrode at the passive state potential is measured, and said pulse voltage signal is applied when said passive state keeping current density is changed to 0.1 mA/cm$^2$ or below.

16. A method of measuring the corrosion degree of a material being measured according to claim 1, wherein the pulse width of said pulse voltage signal ranges from one second to five seconds.

17. A method of measuring the corrosion degree of a material being measured according to claim 1, wherein said passive state potential lies on the anodic side of 0.400 V vs. SHE.

18. A method of measuring the corrosion degree of a material being measured according to claim 1, wherein the peak potential of said pulse voltage signal changing in said cathodic direction is 0.100±0.100 V vs. SHE.

19. A method of measuring the corrosion degree of a material being measured according to claim 1, wherein said electrolytic solution contains at least any one of a sulfuric acid, nitric acid, hydrochloric aid, perchloric acid, chloric acid, hypochlorous acid, acetic acid, thiocyan acid, cyanic acid, salts thereof, carbonate, ammonium, ammonium salt, and hydroxide of metal.

20. A method of measuring the corrosion degree of a material being measured, comprising the steps of immersing a metal electrode made of said material being measured and a counter electrode disposed so as to face said metal electrode in an electrolytic solution, applying a voltage to said metal electrode, measuring a value relating a current flowing between said metal electrode and said counter electrode, and determining the corrosion degree of said material being measured, wherein all of one of the following steps (a) and steps (b) are effected;

wherein the step of applying a voltage includes one of:
(a) applying a voltage across said material made of metal and said counter electrode which are in contact with the electrolytic solution, so that the potential of said material is kept at a passive state potential at which said material being measured reaches a passive state region, and applying a pulse voltage to said material being measured which said material is kept at said passive state potential, said passive state potential being a reference potential; and
(b) applying a voltage changing in a predetermined direction to said metal electrode which said metal electrode is at an initial potential when said metal electrode is immersed in the electrolytic solution, so that the potential of said metal electrode is raised from said initial potential which is a corrosion potential up to a passive state potential at which said metal electrode made of said material being measured reaches a passive state region and is kept at said passive state potential, and stepwise changing said potential of said metal electrode up to a predetermined potential which lies between said initial potential and said passive state potential;

wherein the step of measuring includes one of:
(a) measuring a signal relating to the current flowing between said material being measured and said counter electrode; and (b) measuring the time in which the value of the current flowing between said metal electrode and said counter electrode reaches a constant value; and wherein the step of determining includes one of:
(a) determining the corrosion extent of said material from the measurement of the signal relating to the current flowing between said material being measured and said counter electrode; and
(b) determining the corrosion degree of said material from said time.

21. A method of measuring the corrosion degree of a material being measured according to claim 20, wherein all of the steps (b) are effected.

22. A method of measuring the corrosion degree of a material being measured according to claim 21, wherein said time measured for said material and said time measured for a reference material having a known intergranular corrosion degree are compared with each other to determine the intergranular corrosion degree of said material being measured.

23. A method of measuring the corrosion degree of a material being measured according to claim 22, wherein said reference material is a solution-annealed material.

24. A method of measuring the corrosion degree of a material being measured according to claim 21, wherein after the potential of said metal electrode is raised up to said passive state potential, it is kept at said passive state potential for at least 60 seconds until said pulse voltage signal is applied.

25. A method of measuring the corrosion degree of a material being measured according to claim 21, wherein after the potential of said metal electrode is raised up to said passive state potential, the current density for keeping said metal electrode at the passive state potential is measured, and said pulse voltage signal is applied when said passive state keeping current density is changed to 0.1 mA/cm$^2$ or below.

26. A method of measuring the corrosion degree of a material being measured according to claim 21, wherein the measured intensity of said current is divided by the surface area of said metal electrode so that a current density is calculated, and the corrosion degree of said material being measured is determined from said current density.

27. A method of measuring the corrosion degree of a material being measured according to claim 26, wherein the peak potential of said pulse voltage signal changing in said cathodic direction is 0.100±0.100 V vs. SHE.

28. A method of measuring the corrosion degree of a material being measured according to claim 21 or 26, wherein said electrolytic solution contains at least any one of a sulfuric acid, nitric acid, hydrochloric acid, perchloric acid, chloric acid, hypochlorous acid, acetic acid, thiocyan acid, cyanic acid, salts thereof, carbonate, ammonium, ammonium salt, and hydroxide of metal.

29. A method of measuring the corrosion degree of a material being measured according to claim 21, wherein said predetermined constant current value ranges from 0.1 mA/cm$^3$ to 1 mA/cm$^3$.

30. A method of measuring the corrosion degree of a material being measured according to claim 21, wherein said predetermined potential between said initial potential and said passive state potential is 0.100± 0.100 V vs. SHE.

31. A method of measuring the corrosion degree of a material being measured according to claim 21, wherein said passive state potential lies on the anodic side of 0.400 V vs. SHE.

32. A method of measuring the corrosion degree of a material being measured by immersing a metal electrode made of said material being measured and a counter electrode disposed so as to face said metal electrode in an electrolytic solution, applying a voltage to said metal electrode, measuring a current flowing between said metal electrode and said counter electrode, and determining the corrosion degree of said material being measured, comprising the steps of:

applying a voltage changing in an anodic direction to said metal electrode which is at an initial potential when said metal electrode is immersed in said electrolytic solution, so that the potential of said metal electrode is raised from said initial potential which is a corrosion potential up to a passive state potential at which said metal electrode made of said material being measured reaches a passive state region, and is kept at said passive state potential;

applying a pulse voltage signal which changes in a cathodic direction and of which the peak potential lies in an active state region to said metal electrode which is kept at said passive state potential as a reference potential, and measuring the intensity of a current flowing between said metal electrode and said counter electrode when said pulse voltage is applied in said cathodic direction;

applying a pulse signal which changes in an anodic direction and of which the peak potential lies in a transpassive state region to said metal electrode which is kept at said passive state potential as said reference potential, and measuring the intensity of a current flowing between said metal electrode and said counter electrode when said pulse voltage is applied in said anodic direction;

comparing said value of said current measured for said material being measured when said pulse voltage is applied in said cathodic direction, and said value of said current measured for a reference material having a known sensitization degree when said pulse voltage is applied in said cathodic direction so as to determine the sensitization degree of said material being measured; and comparing said value of said current measured for said material being measured when said pulse voltage is applied in said anodic direction, and said value of said current measured for a reference material having a known intergranular corrosion degree when said pulse voltage is applied in said anodic direction so as to determine the intergranular corrosion degree of said material being measured.

33. A method of measuring the corrosion degree of a material being measured according to claim 32, wherein a quantity of electricity is determined from said current value and the corrosion degree is determined from said amount of electricity.

34. A method of measuring the corrosion degree of a material being measured according to claim 32, wherein after the potential of said metal electrode is raised up to said passive state potential, it is kept at said passive state potential for at least 60 seconds until said pulse voltage signal is applied.

35. A method of measuring the corrosion degree of a material being measured according to claim 32, wherein after the potential of said metal electrode is raised up to said passive state potential, the current density for keeping said metal electrode at the passive state potential is measured, and said pulse voltage signal is applied when said passive state keeping current density is changed to 0.1 mA/cm$^2$ or below.

36. A method of measuring the corrosion degree of a material being measured according to claim 32, wherein the pulse width of said pulse voltage signal ranges from one second to five seconds.

37. A method of measuring the corrosion degree of a material being measured according to claim 32, wherein said passive state potential lies on the anodic side of 0.400 V vs. SHE.

38. A method of measuring the corrosion degree of a material being measured according to claim 32, wherein said reference material is a solution-annealed material.

39. A method of measuring the corrosion degree of a material being measured by immersing a metal electrode made of said material being measured and a counter electrode disposed so as to face said metal electrode in an electrolytic solution, applying a voltage to said metal electrode, measuring a current flowing between said metal electrode and said counter electrode, and determining the corrosion degree of said material being measured, comprising the steps of:

applying a voltage changing in an anodic direction to said metal electrode which is at an initial potential when said metal electrode is immersed in said electrolytic solution, so that the potential of said metal electrode is raised from said initial potential which is a corrosion potential up to a passive state potential at which said metal electrode made of said material being measured reaches a passive state region, and kept at said passive state potential;

applying a pulse signal which changes in an anodic direction and of which the peak potential lies in a transpassive state region to said metal electrode which is kept at said passive state potential as a reference potential, and measuring the intensity of a current flowing between said metal electrode and said counter electrode when said pulse voltage is applied in said anodic direction; and comparing said value of said current measured for said material being measured when said pulse voltage is applied in said anodic direction, and said value of said current measured for a reference material having a known intergranular corrosion degree when said pulse voltage is applied in said anodic direction so as to determine the intergranular corrosion degree of said material being measured.

40. A method of measuring the corrosion degree of a material being measured according to claim 39, wherein a quantity of electricity is determined from said current value and the corrosion degree is determined from said quantity of electricity.

41. A method of measuring the corrosion degree of a material being measured according to claim 39, wherein after the potential of said metal electrode is raised up to said passive state potential, it is kept at said passive state potential for at least 60 seconds until said pulse voltage signal is applied.

42. A method of measuring the corrosion degree of a material being measured according to claim 39, wherein after the potential of said metal electrode is raised up to said passive state potential, the current density for keeping said metal electrode at the passive state potential is measured, and said pulse voltage signal is applied when said passive state keeping current density is changed to 0.1 mA/cm$^2$ or below.

43. A method of measuring the corrosion degree of a material being measured according to claim 39, wherein the pulse width of said pulse voltage signal ranges from one second to five seconds.

44. A method of measuring the corrosion degree of a material being measured according to claim 39, wherein said passive state potential lies on the anodic side of 0.400 V vs. SHE.

45. A method of measuring the corrosion degree of a material being measured according to claim 39, wherein said reference material is a solution-annealed material.

46. A method of measuring the corrosion extent of a material made of metal being measured, comprising the steps of:
applying a voltage across said material made of metal and a counter electrode disposed so as to face said material made of metal which are in contact with a desired electrolytic solution, so that the potential of said material is kept at a passive state potential at which said material being measured reaches a passive state region;
applying a pulse voltage to said material being measured which said material is kept at said passive state potential, said passive state potential being a reference potential; and
determining the corrosion extent of said material from measurement of a signal relating to a current flowing between said material being measured and said counter electrode.

47. A method of measuring the corrosion extent of a material made of metal being measured, according to claim 46, wherein the signal relating to a current is the intensity of the current.

48. A method of measuring the corrosion extent of a material being measured, according to claim 47, wherein a current density obtained for said material being measured is compared with a current density previously measured for a reference material having a known sensitization degree so as to find the intergranular corrosion extent, stress corrosion cracking sensitivity or sensitization degree of said material being measured.

49. A method of measuring the corrosion extent of a material being measured, according to claim 46 or 48, wherein a pulse voltage changing in an anodic direction from an initial potential of said material as said reference to said passive state potential is applied to said material which is kept at a corrosion potential, a current flowing between said material and the counter electrode is measured, and a ratio between the intensity of a current flowing when said voltage is applied in said anodic direction and the intensity of a current flowing when said voltage is applied in a cathodic direction is determined and used to find the corrosion extent of said material being measured.

50. A method of measuring the corrosion extent of a material made of metal being measured, comprising the steps of:
applying a voltage which changes in an anodic direction across said material made of metal and a counter electrode disposed so as to face said material made of metal which are in contact with an electrolytic solution so that said material is kept at an initial potential before said voltage is applied, thereby raising the potential of said material from said initial potential up to a passive state potential at which said material can reach a passive state region, and keeping said material at said passive state potential; and
applying a pulse voltage signal across said material and said counter electrode in a cathodic direction so as to provide a potential which is previously set between said initial potential and said passive state potential, at which time the corrosion extent of said material being measured is determined on the basis of the time in which the current flowing between said material and said counter electrode reaches a certain constant value.

51. A method of measuring the corrosion extent of a material made of metal being measured, comprising the steps of:
applying a voltage which changes in an anodic directions to said material made of metal and a counter electrode disposed to face said material made of metal which are in contact with an electrolytic solution so that said material is kept at an initial potential before said voltage is applied, thereby raising the potential of said material from said initial potential up to a passive state potential at which said material can reach a passive state region, and keeping said material at said passive state potential;
applying a pulse voltage which changes in a cathodic direction and of which the peak potential lies in an active state region to said material which is kept at said passive state potential as a reference potential, and measuring the intensity of a current flowing between said material being measured and said counter electrode when said pulse voltage is applied in said cathodic direction;
applying a pulse voltage which changes in an anodic direction and of which the peak potential lies in an transpassive state region to said material which is kept at said passive state potential as a reference potential, and measuring the intensity of a current flowing between said material being measured and said counter electrode when said pulse voltage is applied in said anodic direction;
comparing said value of said current measured for said material being measured when said pulse voltage is applied in said cathodic direction, and said value of said current previously measured for a reference material having a known sensitization degree when said pulse voltage is applied in said cathodic direction so as to determine the sensitization degree of said material being measured; and
comparing said value of said current measured for said material being measured when said pulse voltage is applied in said anodic direction, and said value of said current previously measured for a reference material having a known intergranular corrosion degree when said pulse voltage is applied in said anodic direction so as to determine the intergranular corrosion degree of said material being measured.

52. A method of measuring the corrosion extent of a material made of metal being measured, comprising the steps of:
applying a voltage which changes in an anodic direction, to said material made of metal and a counter electrode disposed to face said material made of metal which are in contact with an electrolytic solution so that said material is kept at an initial potential before said voltage is applied, thereby raising the potential of said material from said initial potential up to a passive state potential at which said material can reach a passive state region, and keeping said material at said passive state potential;
applying a pulse voltage which changes in an anodic direction and of which the peak potential lies in a transpassive state region to said material which is kept at said passive state potential as a reference potential, and measuring the intensity of a current flowing between said material being measured and said counter electrode when said pulse voltage is applied in said anodic direction; and comparing said value of said current measured for said material being measured when said pulse voltage is applied in said anodic direction, and said value of said current previously measured for a reference material having a known intergranular corrosion degree when said pulse voltage is applied in said anodic direction so as to determine the intergranular corrosion degree of said material being measured.

53. A corrosion degree measuring apparatus for measuring the corrosion degree of a metal material of which an object is made on the wall surface of said object, comprising:

a container having an opening through which an electrolytic solution is made in contact with the wall surface of said object and inlets through which said electrolytic solution is injected into said container;

an electrolytic solution holder which is connected to said inlets of said container and which holds said electrolytic solution which is to be injected into said container;

injection means for injecting said electrolytic solution held within said solution holder into said container in response to a command from the external;

fixing means for pushing said opening of said container against the wall surface of said object so as to fix said container in response to a command from the external;

a terminal which is disposed around said opening of said container and which is made in electric contact with said wall surface when said fixing means pushes said opening of said container against said wall surface of said object;

a counter electrode and reference electrode which are disposed within said container and which are electrically connected to said terminal;

voltage applying means for applying a voltage pulse between said wall surface made in contact with said terminal and said counter electrode such that a passive state potential of said metal material is first applied to said metal material and then an active state region..potential or a transpassive state region potential of said metal material is applied to said metal material; and current detecting means for detecting a current flowing between said wall surface made in contact with said terminal and said counter electrode.

54. A scanning tunneling microscope comprising:

a probe holder for holding a probe in an electrolytic solution;

a sample table for holding a sample in said electrolytic solution;

voltage applying means for applying a voltage between said probe and said sample;

scanning means for causing said probe to scan the surface of said sample; and current detecting means for detecting a current flowing between said probe and said sample, wherein said voltage applying means has pulse voltage applying means for applying a pulse voltage so that a passive state potential of said sample is first obtained and then an active state potential or a transpassive state potential of said sample is obtained and calculating means for calculating the corrosion degree of said sample from the detected results which can be obtained from said current detecting means when said pulse voltage is applied.

55. A method for measuring a corrosion degree of a material based on an amount of a current flowing between a counter electrode and a metal electrode made of said material which is electrically connected to both said counter electrode through a voltage applying part and a current measurement part in series and a reference electrode through a potential difference measurement part, said method comprising the steps of:

immersing said metal electrode, said counter electrode and said reference electrode in a desired electrolyte;

applying a voltage across said metal electrode and said counter electrode so that a potential difference between said reference electrode and said metal electrode or an electrode potential of said metal electrode relative to said reference electrode measured by said potential difference measurement part reach a desired value using said voltage applying part, wherein the step of applying a voltage includes changing the electrode potential of said metal electrode relative to the potential of said reference electrode to a potential in a potential region where said metal electrode presents passivation, holding said potential in the potential region, said potential held representing an initial potential, applying to said metal electrode a plurality of potentiostatic pulse signals each having a different potential relative to said initial potential;

measuring a current flowing between said counter electrode and said metal electrode, when said voltage is applied; and determining the corrosion degree of said material, based on an intensity of said current measured.

56. A method according to claim 55, wherein said plurality of potentiostatic pulse signals have different pulse potentials in at least one of (1) in a cathodic direction, (2) an anodic direction and (3) both anodic and cathodic directions, respectively, relative to said initial potentials.

* * * * *